US012729189B2

(12) United States Patent
Bucknell et al.

(10) Patent No.: US 12,729,189 B2
(45) Date of Patent: Sep. 8, 2026

(54) GPR52 MODULATOR COMPOUNDS

(71) Applicant: NXERA PHARMA UK LIMITED, Cambridge (GB)

(72) Inventors: Sarah Joanne Bucknell, Cambridge (GB); Stephen Paul Watson, Cambridge (GB); Michael Alistair O'Brien, Cambridge (GB)

(73) Assignee: NXERA PHARMA UK LIMITED, Cambridgeshire (GB)

( * ) Notice: Subject to any disclaimer, the term of this patent is extended or adjusted under 35 U.S.C. 154(b) by 712 days.

(21) Appl. No.: 18/023,411

(22) PCT Filed: Aug. 31, 2021

(86) PCT No.: PCT/GB2021/052247
§ 371 (c)(1),
(2) Date: Feb. 27, 2023

(87) PCT Pub. No.: WO2022/043714
PCT Pub. Date: Mar. 3, 2022

(65) Prior Publication Data

US 2023/0348416 A1 Nov. 2, 2023

(30) Foreign Application Priority Data

Aug. 28, 2020 (GB) ...................................... 2013558

(51) Int. Cl.

| | |
|---|---|
| ***C07D 401/04*** | (2006.01) |
| ***A61K 31/4439*** | (2006.01) |
| ***C07D 405/14*** | (2006.01) |
| ***C07D 491/04*** | (2006.01) |
| ***C07D 491/044*** | (2006.01) |
| *A61P 25/18* | (2006.01) |

(52) U.S. Cl.
CPC ......... *C07D 401/04* (2013.01); *C07D 405/14* (2013.01); *C07D 491/04* (2013.01)

(58) Field of Classification Search
CPC ... C07D 401/04; C07D 405/14; C07D 491/04
See application file for complete search history.

(56) References Cited

FOREIGN PATENT DOCUMENTS

| | | | |
|---|---|---|---|
| KR | 10-2010-0097077 | A | 9/2010 |
| RU | 2018 112 230 | A | 10/2019 |
| WO | WO 2005/037797 | A1 | 4/2005 |
| WO | WO 2016/176571 | A1 | 11/2016 |
| WO | WO 2017/050792 | A1 | 3/2017 |
| WO | WO 2017/077280 | A1 | 5/2017 |
| WO | WO 2018/098561 | A1 | 6/2018 |
| WO | WO 2019/053090 | A1 | 3/2019 |
| WO | WO2019/079485 | A1 | 4/2019 |
| WO | WO 2019/079596 | A1 | 4/2019 |
| WO | WO 2019/079607 | A1 | 4/2019 |
| WO | WO 2021/090030 | A1 | 5/2021 |

OTHER PUBLICATIONS

Guo et al. Identification, Synthesis, and Pharmacological Evaluation of Tetrahydroindazole Based Ligands as Novel Antituberculosis Agents J Med Chem 2010 53, 649-659 (Year: 2010).*

Komatsu et al., "Anatomical Transcriptome of G Protein-Coupled Receptors Leads to the Identification of a Novel Therapeutic Candidate GPR52 for Psychiatric Disorders," PLOS ONE, vol. 9, Issue 2, Feb. 2014, e90134, pp. 1-16.

Tokumaru et al., "Design, synthesis, and pharmacological evaluation of 4-azolyl-benzamide derivatives as novel GPR52 agonists," Bioorganic & Medicinal Chemistry, vol. 25, 2017 (Available online Apr. 1, 2017), pp. 3098-3115.

International Search Report, issued in PCT/GB2021/052247, dated Oct. 12, 2021.

Written Opinion of the International Searching Authority, issued in PCT/GB2021/052247, dated Oct. 12, 2021.

* cited by examiner

*Primary Examiner* — Bruck Kifle
*Assistant Examiner* — Kevin S Martin
(74) *Attorney, Agent, or Firm* — Birch, Stewart, Kolasch & Birch, LLP

(57) ABSTRACT

The disclosures herein relate to novel compounds of Formula (1): or a salt thereof, wherein Q, V, L, W, $R^1$ and $R^2$ are defined herein, and their use in treating, preventing, ameliorating, controlling or reducing the risk of disorders associated with GPR52 receptors.

(1)

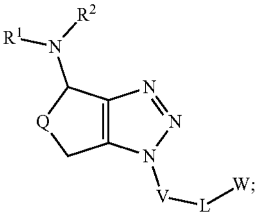

38 Claims, 1 Drawing Sheet

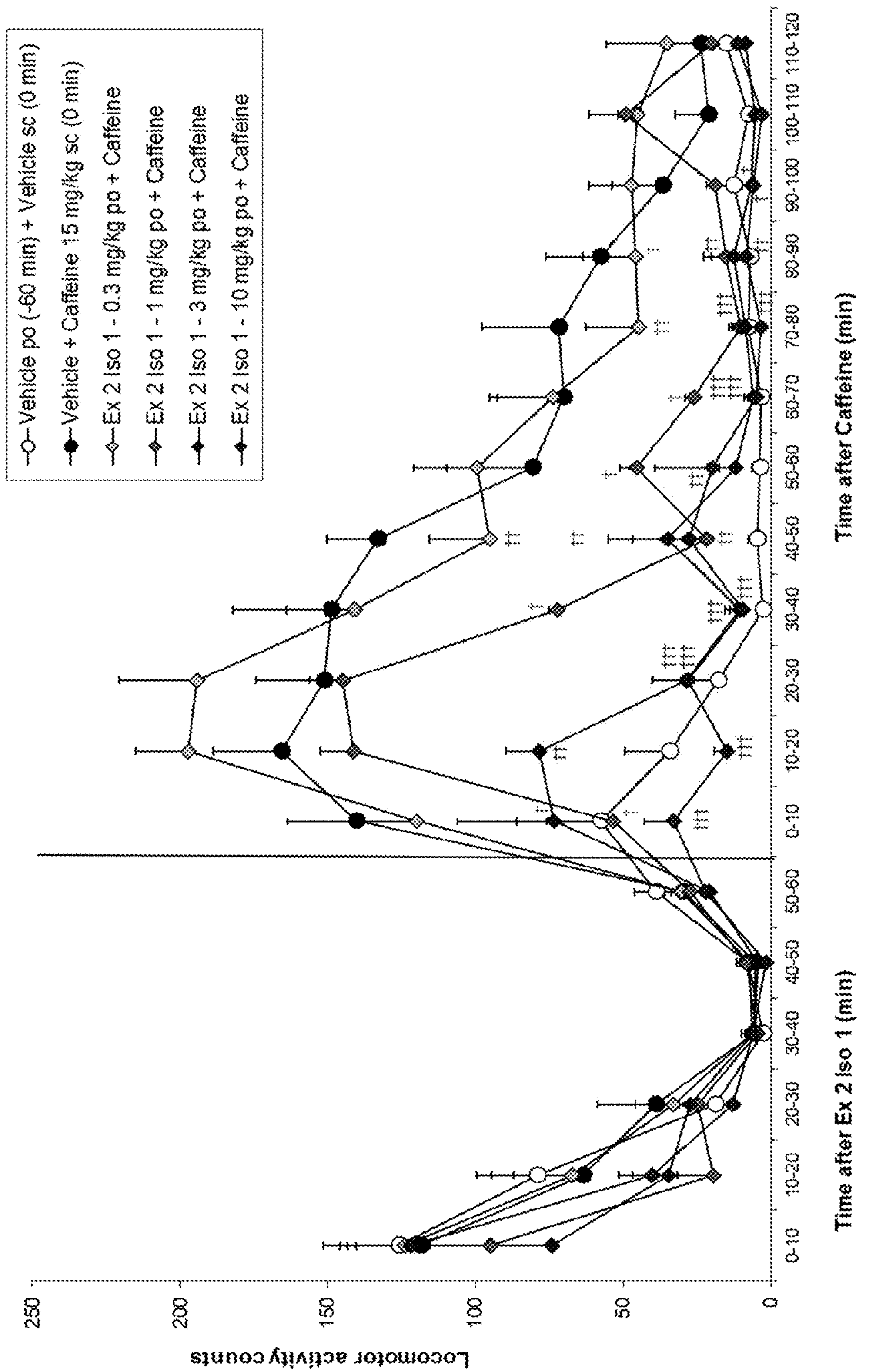
Vehicle po (-60 min) + Vehicle sc (0 min)
Vehicle + Caffeine 15 mg/kg sc (0 min)
Ex 2 Iso 1 - 0.3 mg/kg po + Caffeine
Ex 2 Iso 1 - 1 mg/kg po + Caffeine
Ex 2 Iso 1 - 3 mg/kg po + Caffeine
Ex 2 Iso 1 - 10 mg/kg po + Caffeine
Locomotor activity counts
250
200
150
100
50
0
Time after Ex 2 Iso 1 (min)
Time after Caffeine (min)
0-10
10-20
20-30
30-40
40-50
50-60
60-70
70-80
80-90
90-100
100-110
110-120

GPR52 MODULATOR COMPOUNDS

This application relates to novel compounds and their use as G-protein coupled receptor 52 (GPR52) modulators. Compounds described herein may be useful in the treatment or prevention of diseases in which GPR52 receptors are involved or in which modulation of GPR52 receptors may be beneficial. The application is also directed to pharmaceutical compositions comprising these compounds and the manufacture and use of these compounds and compositions in the prevention or treatment of such diseases in which GPR52 receptors are involved.

BACKGROUND OF THE INVENTION

G-protein coupled receptor 52 (GPR52) is a constitutively active Gs coupled orphan receptor which is highly expressed in the striatum and cortex. In the striatum GPR52 is expressed exclusively on dopamine D2 medium spiny neurons and in the cortex it is found on cortical pyramidal neurons expressing dopamine D1 receptors (Komatsu et al, 2014, PLoS One 9:e90134). Based on its localization and functional coupling, GPR52 is proposed to play a role in the modulation of fronto-striatal and limbic dopamine and may therefore have utility in the treatment of neuropsychiatric disorders. GPR52 agonists are thought to be particularly relevant to the treatment of schizophrenia, where they are hypothesized to improve cognition and negative symptoms indirectly by potentiating D1 signalling but alleviate positive symptoms through inhibition of D2-mediated signalling in the striatum.

GPR52 agonists could be used to treat psychiatric disorders related to dysfunction of the mesolimbic and mesocortical pathways. Examples include treatment of the positive, negative and cognitive symptoms of schizophrenia, depression, attention-deficit hyperactivity disorder, anxiety disorders (generalised anxiety disorder, obsessive compulsive disorder, panic disorder), bipolar disorder, addiction/impulse-control disorders and autism spectrum disorders. Neuropsychiatric symptoms (e.g. psychosis, anhedonia, agitation, etc) of neurodegenerative diseases (e.g. Alzheimer's disease, Parkinson's disease, Huntington's disease, etc) could also be treated by GPR52 agonists. GPR52 expression in the pituitary gland and hypothalamus suggests utility for GPR52 modulators in pituitary and hypothalamic disorders, and there is preclinical evidence (Xiong et al, 2016, WO2016/176571) to suggest that GPR52 agonists could be useful in the treatment of hyperprolactinemia.

THE INVENTION

The present invention provides compounds having activity as G protein-coupled receptor 52 (GPR52) modulators.

Provided is a compound of Formula (1):

(1)

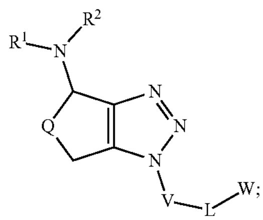

or a salt thereof, wherein;

$R^1$ is H, $C(O)C_{1-3}$ alkyl optionally substituted with 1 to 6 fluorine atoms, $C_{1-6}$ alkyl optionally substituted with 1 to 6 fluorine atoms or $C_{3-6}$ cycloalkyl optionally substituted with 1 to 6 fluorine atoms; wherein any one atom of the alkyl or cycloalkyl groups may be optionally replaced by O;

$R^2$ is H or $C_{1-3}$ alkyl optionally substituted with 1 to 6 fluorine atoms; Q is selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$;

$R^3$, $R^4$, $R^5$, $R^6$, $R^7$ and $R^3$ are independently selected from H and $C_{1-3}$ alkyl;

V is a 6-membered optionally substituted aryl or heteroaryl ring substituted with L at the meta-position;

L is selected from $CH_2$, CHOH and O;

and W is a 6-membered optionally substituted aryl or heteroaryl ring.

Compounds of the present invention may be used as GPR52 modulators. Compounds of the present invention may be used as GPR52 agonists. Compounds of the present invention may be used in the manufacture of medicaments. The compounds or medicaments may be for use in treating, preventing, ameliorating, controlling or reducing the risk of diseases or disorders in which GPR52 receptors are involved. The compounds or medicaments may be for use in treating, preventing, ameliorating, controlling or reducing the risk of diseases or disorders in which modulation of GPR52 receptors may be beneficial. Compounds of the present invention may be useful in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; hypothalamic disorders; pituitary disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

Compounds of the present invention may be useful in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, anhedonia, agitation, Alzheimer's disease, Parkinson's disease, Huntington's disease, vascular dementia, Lewy body disease, frontotemporal dementia, Tourette's syndrome, hyperprolactinemia, pituitary adenoma, prolactinoma, craniopharyngioma, Cushing's disease, diabetes insipidus, non-functioning tumours, obesity, posttraumatic stress disorder (PTSD), akathisia and associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, schizotypal personality disorder, delusional disorder, brief psychotic disorder, schizophreniform disorder, schizoaffective disorder, substance- or medication-induced psychotic disorder, delusions, hallucinations, disorganized thinking, grossly disorganized or abnormal motor behavior, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorders due to another medical condition, delirium, major neurocognitive disorder, minor neurocognitive disorder, amnesia, dementia, developmental coordination disorder, stereotypic movement disorder, a post-stroke effect, dentatorubral-pallidoluysian atrophy, diminished emotional expression, avolition, alogia and asociality.

DETAILED DESCRIPTION OF THE INVENTION

The invention relates to novel compounds. The invention also relates to the use of novel compounds as modulators of the GPR52 receptor. The invention further relates to the use of novel compounds in the manufacture of medicaments for use as GPR52 modulators. Compounds of the present invention may be used as GPR52 agonists. The compounds or medicaments may be for use in treating, preventing, ameliorating, controlling or reducing the risk of diseases or disorders in which GPR52 receptors are involved. The compounds or medicaments may be for use in treating, preventing, ameliorating, controlling or reducing the risk of diseases or disorders in which modulation of GPR52 receptors may be beneficial.

The invention further relates to compounds, compositions and medicaments that may be useful in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

Provided is a compound of Formula (1):

(1)

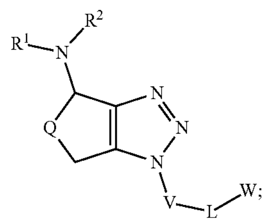

or a salt thereof, wherein;

$R^1$ is H, $C(O)C_{1-3}$ alkyl optionally substituted with 1 to 6 fluorine atoms, $C_{1-6}$ alkyl optionally substituted with 1 to 6 fluorine atoms or $C_{3-6}$ cycloalkyl optionally substituted with 1 to 6 fluorine atoms; wherein any one atom of the alkyl or cycloalkyl groups may be optionally replaced by O;

$R^2$ is H or $C_{1-3}$ alkyl optionally substituted with 1 to 6 fluorine atoms;

Q is selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$;

$R^3$, $R^4$, $R^5$, $R^6$, $R^7$ and $R^3$ are independently selected from H and $C_{1-3}$ alkyl;

V is a 6-membered optionally substituted aryl or heteroaryl ring substituted with L at the meta-position;

L is selected from $CH_2$, CHOH and O;

and W is a 6-membered optionally substituted aryl or heteroaryl ring.

Also provided is a compound of Formula (Ia):

(1a)

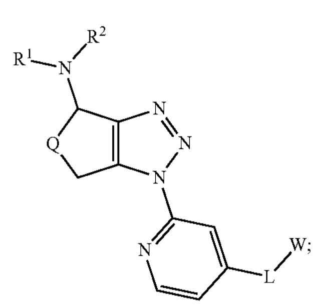

or a salt thereof, wherein;

$R^1$ is H, $C(O)C_{1-3}$ alkyl optionally substituted with 1 to 6 fluorine atoms, $C_{1-6}$ alkyl optionally substituted with 1 to 6 fluorine atoms or $C_{3-6}$ cycloalkyl optionally substituted with 1 to 6 fluorine atoms; wherein any one atom of the alkyl or cycloalkyl groups may be optionally replaced by O;

$R^2$ is H or $C_{1-3}$ alkyl optionally substituted with 1 to 6 fluorine atoms;

Q is selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$;

$R^3$, $R^4$, $R^5$, $R^6$, $R^7$ and $R^3$ are independently selected from H and $C_{1-3}$ alkyl;

L is selected from $CH_2$, CHOH and O;

and W is a 6-membered optionally substituted aryl or heteroaryl ring.

Also provided is a compound of Formula (1a):

(1a)

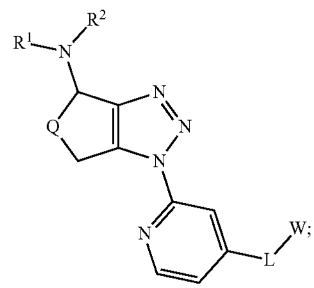

or a salt thereof, wherein;

$R^1$ is H, $C(O)C_{1-3}$ alkyl optionally substituted with 1 to 6 fluorine atoms, $C_{1-6}$ alkyl optionally substituted with 1 to 6 fluorine atoms or $C_{3-6}$ cycloalkyl optionally substituted with 1 to 6 fluorine atoms; wherein any one atom of the alkyl or cycloalkyl groups may be optionally replaced by O;

$R^2$ is H;

Q is selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$;

$R^3$, $R^4$, $R^5$, $R^6$, $R^7$ and $R^8$ are independently selected from H and $C_{1-3}$ alkyl; L is selected from $CH_2$, CHOH and O;

and W is a 6-membered optionally substituted aryl or heteroaryl ring.

In the compounds herein, $R^1$ can be selected from H, $CH_3$, $CF_3$, $CHF_2$, $CH_2F$, $C(O)CH_3$, $C(O)CH_2CH_3$, $C(O)CF_2H$, $C(O)CF_3$, $C(O)CFH_2$, $CH_2CH_2OCH_3$, oxetane and oxolane. $R^1$ can be selected from H, $CH_3$, $C(O)CH_3$, $C(O)CH_2CH_3$, $C(O)CF_2H$, $C(O)CF_3$, $C(O)CFH_2$, $CH_2CH_2OCH_3$, oxetane and oxolane. $R^1$ can be $C(O)CH_3$.

In the compounds herein, $R^2$ can be selected from H, $CH_3$, $CF_3$, $CHF_2$ and $CH_2F$. $R^2$ can be H.

In the compounds herein, Q can be selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$, wherein $R^3$, $R^4$, $R^5$, $R^6$, $R^7$ and $R^8$ are H. Q can be selected from $—CH_2—$, $—CH_2CH_2—$, $—CH_2CH_2CH_2—$, $—CH_2CH_2O—$, $—CH_2OCH_2—$ and $—CH_2O—$. Q can be $—CH_2CH_2—$.

In the compounds herein, L can be $CH_2$. L can be CHOH. L can be O.

In the compounds herein, V can be an optionally substituted phenyl or pyridyl ring which is substituted with L at the meta position.

V can be selected from the group consisting of:

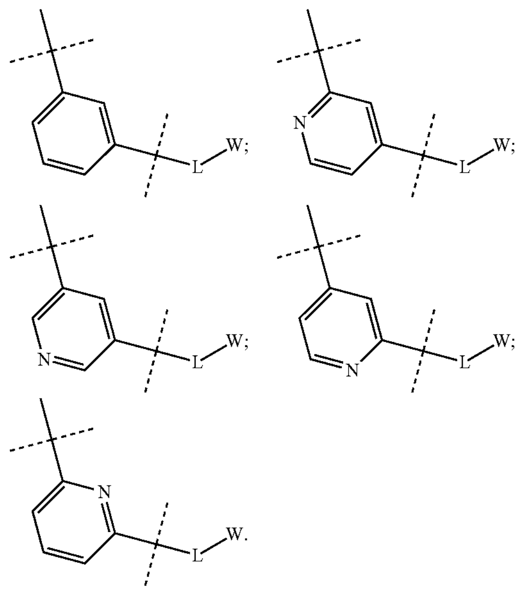

V can be:

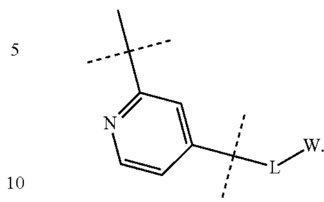

In the compounds herein, W can be:

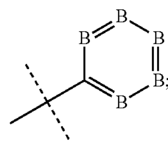

wherein each B is independently selected from N, $CR^{11}$, $CR^{12}$ or $CR^{13}$;

and wherein $R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

W can be a moiety selected from:

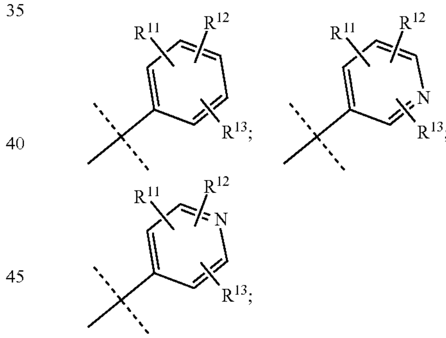

wherein $R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

W can be selected from the group consisting of:

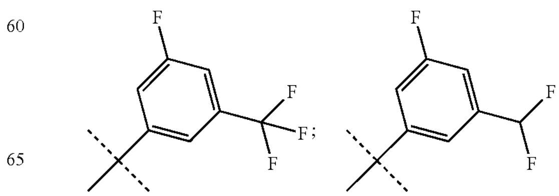

-continued

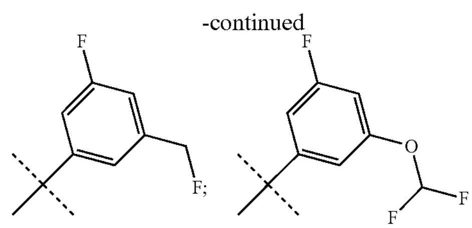

In the compounds herein, $R^{11}$, $R^{12}$ and $R^{13}$ can independently be H, CN, F, Cl, methyl, cyclopropyl, $CF_3$, $CF_2H$, $OCF_2H$, $OCF_3$, OMe or $SO_2Me$. $R^{11}$, $R^{12}$ and $R^{13}$ can be independently selected from H, F, $CF_3$, $CF_2H$, $CFH_2$ and $OCF_2H$. $R^{11}$, $R^{12}$ and $R^{13}$ can be independently selected from H, F and $CF_3$.

In the compounds herein, $R^{11}$ can be H. $R^{11}$ can be CN. $R^{11}$ can be halo. $R^{11}$ can be F or Cl. $R^{11}$ can be F. $R^{11}$ can be a $C_{1-6}$ alkyl group which is optionally substituted with 1 to 6 fluorine atoms wherein one atom of the $C_{1-6}$ alkyl group may be optionally replaced by a heteroatom selected from O, N, S and oxidised forms thereof. $R^{11}$ can be a $C_{1-6}$ alkyl group which is optionally substituted with 1 to 6 fluorine atoms. $R^{11}$ can be a $C_{1-6}$ alkyl group. $R^{11}$ can be a $OC_{1-6}$ alkyl group which is optionally substituted with 1 to 6 fluorine atoms. $R^{11}$ can be a $OC_{1-6}$ alkyl group. $R^{11}$ can be a $SO_2C_{1-6}$ alkyl group which is optionally substituted with 1 to 6 fluorine atoms. $R^{11}$ can be a $SO_2C_{1-6}$ alkyl group. $R^{11}$ can be a $C_{3-6}$ cycloalkyl group which is optionally substituted with 1 to 6 fluorine atoms. $R^{11}$ can be a $C_{3-6}$ cycloalkyl group. $R^{11}$ can be H. $R^{11}$ can be CN. $R^{11}$ can be F. $R^{11}$ can be Cl. $R^{11}$ can be methyl. $R^{11}$ can be cyclopropyl. $R^{11}$ can be $CF_3$. $R^{11}$ can be $OCF_2H$. $R^{11}$ can be $SO_2Me$. $R^{11}$ can be $CF_2H$. $R^{11}$ can be $CH_2F$. $R^{11}$ can be OMe. $R^{11}$ can be H, F, $CF_3$, $CF_2H$, $CFH_2$ or $OCF_2H$. $R^{11}$ can be H, F or $CF_3$.

In the compounds herein, $R^{12}$ can be H. $R^{12}$ can be CN. $R^{12}$ can be halo. $R^{12}$ can be F or Cl. $R^{12}$ can be F. $R^{12}$ can be a $C_{1-6}$ alkyl group which is optionally substituted with 1 to 6 fluorine atoms wherein one atom of the $C_{1-6}$ alkyl group may be optionally replaced by a heteroatom selected from O, N, S and oxidised forms thereof. $R^{12}$ can be a $C_{1-6}$ alkyl group which is optionally substituted with 1 to 6 fluorine atoms. $R^{12}$ can be a $C_{1-6}$ alkyl group. $R^{12}$ can be a $OC_{1-6}$ alkyl group which is optionally substituted with 1 to 6 fluorine atoms. $R^{12}$ can be a $OC._6$ alkyl group. $R^{12}$ can be a $SO_2C_{1-6}$ alkyl group which is optionally substituted with 1 to 6 fluorine atoms. $R^{12}$ can be a $SO_2C_{1-6}$ alkyl group. $R^{12}$ can be a $C_{3-6}$ cycloalkyl group which is optionally substituted with 1 to 6 fluorine atoms. $R^{12}$ can be a $C_{3-6}$ cycloalkyl group. $R^{12}$ can be H. $R^{12}$ can be CN. $R^{12}$ can be F. $R^{12}$ can be Cl. $R^{12}$ can be methyl. $R^{12}$ can be cyclopropyl. $R^{12}$ can be $CF_3$. $R^{12}$ can be $OCF_2H$. $R^{12}$ can be $SO_2Me$. $R^{12}$ can be $CF_2H$. $R^{12}$ can be $CH_2F$. $R^{12}$ can be OMe. $R^{12}$ can be H, F, $CF_3$, $CF_2H$, $CFH_2$ or $OCF_2H$. $R^{12}$ can be H, F or $CF_3$.

In the compounds herein, $R^{13}$ can be H. $R^{13}$ can be CN. $R^{13}$ can be halo. $R^{13}$ can be F or C. $R^{13}$ can be F. $R^{13}$ can be a $C_{1-6}$ alkyl group which is optionally substituted with 1 to 6 fluorine atoms wherein one atom of the $C_{1-6}$ alkyl group may be optionally replaced by a heteroatom selected from O, N, S and oxidised forms thereof. $R^{13}$ can be a $C_{1-6}$ alkyl group which is optionally substituted with 1 to 6 fluorine atoms. $R^{13}$ can be a $C_{1-6}$ alkyl group. $R^{13}$ can be a $OC_{1-6}$ alkyl group which is optionally substituted with 1 to 6 fluorine atoms. $R^{13}$ can be a $OC_{1-6}$ alkyl group. $R^{13}$ can be a $SO_2C_{1-6}$ alkyl group which is optionally substituted with 1 to 6 fluorine atoms. $R^{13}$ can be a $SO_2C_{1-6}$ alkyl group. $R^{13}$ can be a $C_{3-6}$ cycloalkyl group which is optionally substituted with 1 to 6 fluorine atoms. $R^{13}$ can be a $C_{3-6}$ cycloalkyl group. $R^{13}$ can be H. $R^{13}$ can be CN. $R^{13}$ can be F. $R^{13}$ can be Cl. $R^{13}$ can be methyl. $R^{13}$ can be cyclopropyl. $R^{13}$ can be $CF_3$. $R^{13}$ can be $OCF_2H$. $R^{13}$ can be $SO_2Me$. $R^{13}$ can be $CF_2H$. $R^{13}$ can be $CH_2F$. $R^{13}$ can be OMe. $R^{13}$ can be H, F, $CF_3$, $CF_2H$, $CFH_2$ or $OCF_2H$. $R^{13}$ can be H, F or $CF_3$.

Particular compounds include compounds of Formula (2a), (2b) or (2c):

(2a)

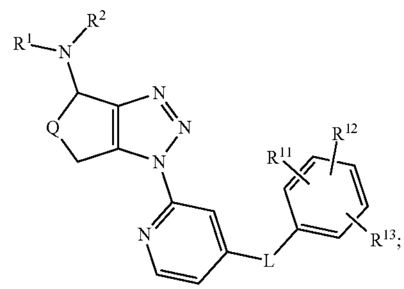

(2b)

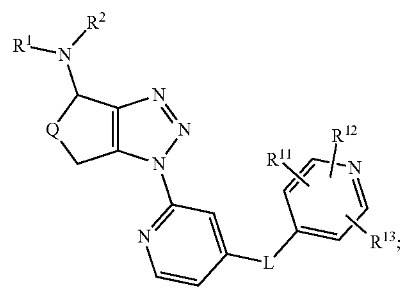

(2c)

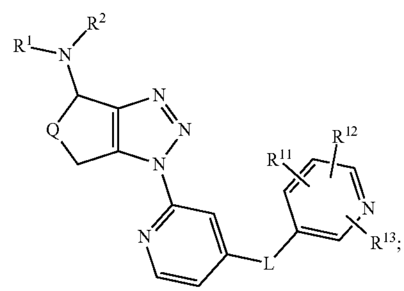

or a salt thereof, wherein Q, L, $R^1$, $R^2$, $R^{11}$, $R^{12}$ and $R^{13}$ are as defined above.

Particular compounds include compounds of Formula (3a), (3b) or (3c):

(3a)

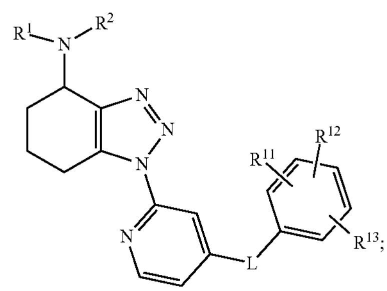

-continued (3b)

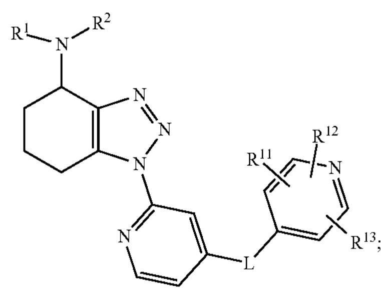

(3c)

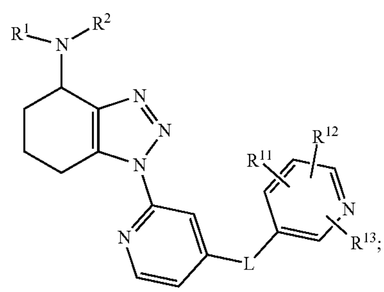

or a salt thereof, wherein L, $R^1$, $R^2$, $R^{11}$, $R^{12}$ and $R^{13}$ are as defined above.

Particular compounds include compounds of Formula (4a), (4b) or (4c):

(4a)

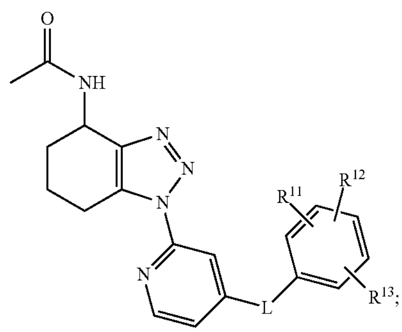

(4b)

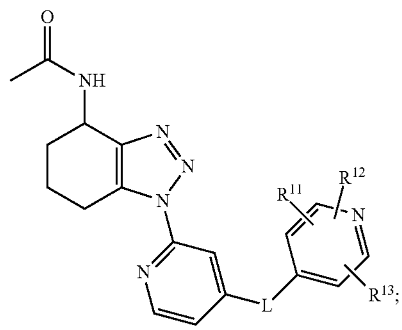

-continued (4c)

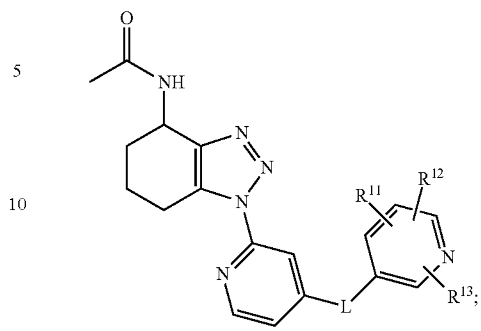

or a salt thereof, wherein L, $R^{11}$, $R^{12}$ and $R^{13}$ are as defined above.

Particular compounds include compounds of Formula (5):

(5)

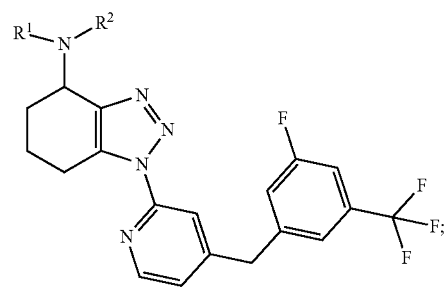

or a salt thereof, wherein $R^1$ and $R^2$ are as defined above.

Particular compounds include compounds of Formula (6a), (6b) or (6c):

(6a)

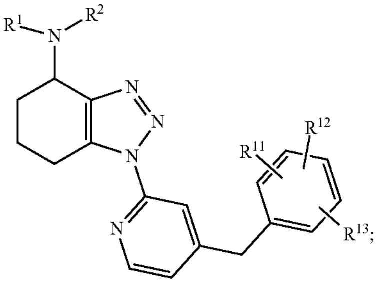

(6b)

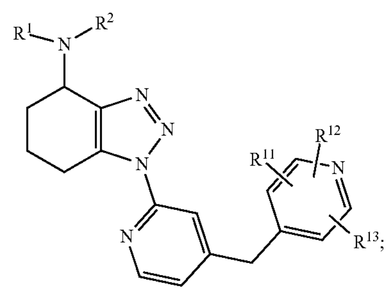

-continued (6c)

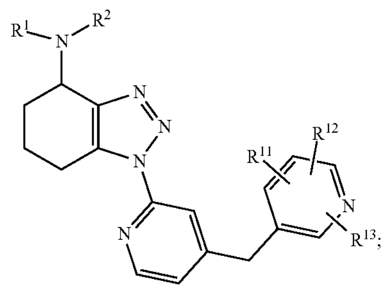

or a salt thereof, wherein $R^1$, $R^2$, $R^{11}$, $R^{12}$ and $R^{13}$ are as defined above.

Particular compounds include compounds of Formula (7a), (7b), (7c), (7d) or (7e):

(7a)

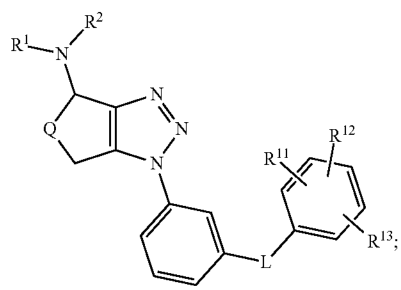

(7b)

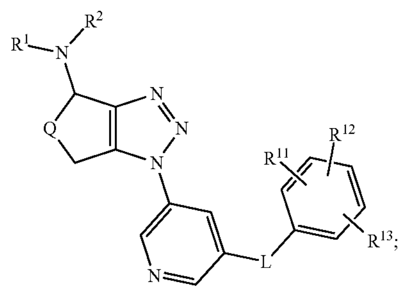

(7c)

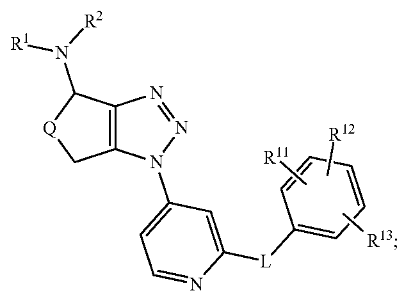

(7d)

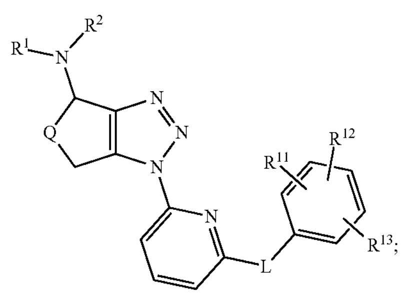

-continued (7e)

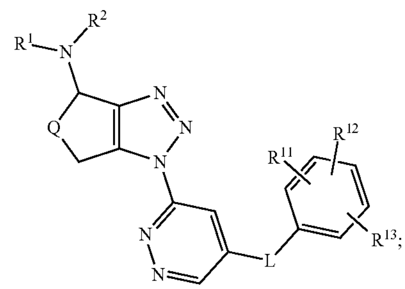

or a salt thereof, wherein Q, L, $R^1$, $R^2$, $R^{11}$, $R^{12}$ and $R^{13}$ are as defined above.

Also included are compounds of Formula (1i) and (1ii):

(1i)

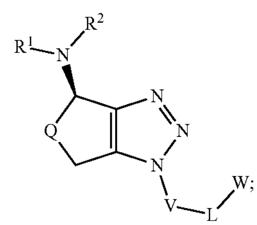

(1ii)

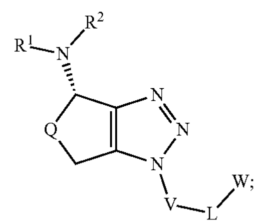

and salts thereof, wherein Q, V, L, W, $R^1$ and $R^2$ are as defined above.

Also included are compounds of Formula (1ai) and (1aii):

(1ai)

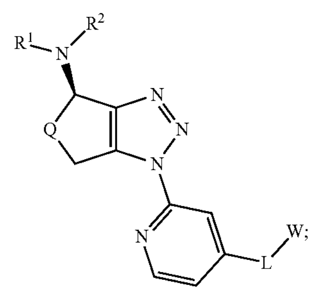

-continued (1aii)

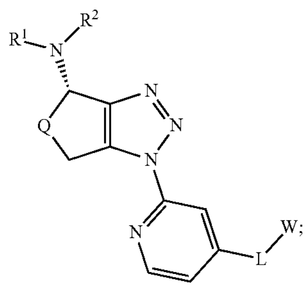

and salts thereof, wherein Q, L, W, $R^1$ and $R^2$ are as defined above.

The compound can be selected from any one of Examples 1 to 21 as shown in Table 1 or a salt thereof.

The compound can be selected from the group consisting of:

1-(4-{[3-fluoro-5-(trifluoromethyl)phenyl]methyl}pyridin-2-yl)-4,5,6,7-tetrahydro-1H-benzotriazol-4-amine;

N-[1-(4-{[3-fluoro-5-(trifluoromethyl)phenyl]methyl}pyridin-2-yl)-4,5,6,7-tetrahydro-1H-benzotriazol-4-yl]acetamide;

N-[1-(4-{[3-fluoro-5-(trifluoromethyl)phenyl]methyl}pyridin-2-yl)-4,5,6,7-tetrahydro-1H-benzotriazol-4-yl]propanamide;

2,2-difluoro-N-[1-(4-{[3-fluoro-5-(trifluoromethyl)phenyl]methyl}pyridin-2-yl)-4,5,6,7-tetrahydro-1H-benzotriazol-4-yl]acetamide;

2-fluoro-N-[1-(4-{[3-fluoro-5-(trifluoromethyl)phenyl]methyl}pyridin-2-yl)-4,5,6,7-tetrahydro-1H-benzotriazol-4-yl]acetamide;

N-(1-{4-[3-fluoro-5-(trifluoromethyl)phenoxy]pyridin-2-yl}-4,5,6,7-tetrahydro-1H-benzotriazol-4-yl)acetamide;

1-(4-{[3-fluoro-5-(trifluoromethyl)phenyl]methyl}pyridin-2-yl)-N-methyl-4,5,6,7-tetrahydro-1H-benzotriazol-4-amine;

1-(4-{[3-fluoro-5-(trifluoromethyl)phenyl]methyl}pyridin-2-yl)-N-(2-methoxyethyl)-4,5,6,7-tetrahydro-1H-benzotriazol-4-amine;

1-(4-{[3-fluoro-5-(trifluoromethyl)phenyl]methyl}pyridin-2-yl)-N-(oxetan-3-yl)-4,5,6,7-tetrahydro-1H-benzotriazol-4-amine;

1-(4-{[3-fluoro-5-(trifluoromethyl)phenyl]methyl}pyridin-2-yl)-N-(oxolan-3-yl)-4,5,6,7-tetrahydro-1H-benzotriazol-4-amine;

N-[1-(4-{[3-(trifluoromethyl)phenyl]methyl}pyridin-2-yl)-4,5,6,7-tetrahydro-1H-benzotriazol-4-yl]acetamide;

N-[1-(4-{[3-(difluoromethoxy)-5-fluorophenyl]methyl}pyridin-2-yl)-4,5,6,7-tetrahydro-1H-benzotriazol-4-yl]acetamide;

N-[1-(4-{[3-(difluoromethyl)-5-fluorophenyl]methyl}pyridin-2-yl)-4,5,6,7-tetrahydro-1H-benzotriazol-4-yl]acetamide;

N-[1-(4-{[3-fluoro-5-(fluoromethyl)phenyl]methyl}pyridin-2-yl)-4,5,6,7-tetrahydro-1H-benzotriazol-4-yl]acetamide;

1-(4-{[3-(difluoromethyl)-5-fluorophenyl]methyl}pyridin-2-yl)-4,5,6,7-tetrahydro-1H-benzotriazol-4-amine;

1-(4-{[3-fluoro-5-(trifluoromethyl)phenyl]methyl}pyridin-2-yl)-1,4,5,6-tetrahydrocyclopenta[d][1,2,3]triazol-4-amine;

N-[1-(4-{[3-fluoro-5-(trifluoromethyl)phenyl]methyl}pyridin-2-yl)-1,4,5,6-tetrahydrocyclopenta[d][1,2,3]triazol-4-yl]acetamide;

3-(4-{[3-fluoro-5-(trifluoromethyl)phenyl]methyl}pyridin-2-yl)-4,6,7,8-tetrahydro-3H-oxepino[3,4-d][1,2,3]triazol-8-amine:

N-[3-(4-{[3-fluoro-5-(trifluoromethyl)phenyl]methyl}pyridin-2-yl)-4,6,7,8-tetrahydro-3H-oxepino[3,4-d][1,2,3]triazol-8-yl]acetamide;

1-(4-{[3-fluoro-5-(trifluoromethyl)phenyl]methyl}pyridin-2-yl)-4,5,7,8-tetrahydro-1H-oxepino[4,5-d][1,2,3]triazol-4-amine;

N-[1-(4-{[3-fluoro-5-(trifluoromethyl)phenyl]methyl}pyridin-2-yl)-4,5,7,8-tetrahydro-1H-oxepino[4,5-d][1,2,3]triazol-4-yl]acetamide;

1-(4-(3-fluoro-5-(trifluoromethyl)phenoxy)pyridin-2-yl)-4,5,6,7-tetrahydro-1H-benzo[d][1,2,3]triazol-4-amine;

1-(4-(3-(trifluoromethyl)benzyl)pyridin-2-yl)-4,5,6,7-tetrahydro-1H-benzo[d][1,2,3]triazol-4-amine;

1-(4-(3-(difluoromethoxy)-5-fluorobenzyl)pyridin-2-yl)-4,5,6,7-tetrahydro-1H-benzo[d][1,2,3]triazol-4-amine;

(4R)-1-(4-{[3-fluoro-5-(trifluoromethyl)phenyl]methyl}pyridin-2-yl)-4,5,6,7-tetrahydro-1H-benzotriazol-4-amine;

(4S)-1-(4-{[3-fluoro-5-(trifluoromethyl)phenyl]methyl}pyridin-2-yl)-4,5,6,7-tetrahydro-1H-benzotriazol-4-amine;

N-[(4R)-1-(4-{[3-fluoro-5-(trifluoromethyl)phenyl]methyl}pyridin-2-yl)-4,5,6,7-tetrahydro-1H-benzotriazol-4-yl]acetamide;

N-[(4S)-1-(4-{[3-fluoro-5-(trifluoromethyl)phenyl]methyl}pyridin-2-yl)-4,5,6,7-tetrahydro-1H-benzotriazol-4-yl]acetamide;

N-[(4R)-1-(4-{[3-(difluoromethyl)-5-fluorophenyl]methyl}pyridin-2-yl)-4,5,6,7-tetrahydro-1H-benzotriazol-4-yl]acetamide;

N-[(4S)-1-(4-{[3-(difluoromethyl)-5-fluorophenyl]methyl}pyridin-2-yl)-4,5,6,7-tetrahydro-1H-benzotriazol-4-yl]acetamide;

or a salt thereof.

Further embodiments of the invention include the use of a compound of Formula (1) or a salt thereof or a pharmaceutical composition comprising a compound of Formula (1) as a GPR52 receptor modulator or a GPR52 receptor agonist. Compounds of the present invention may be used as GPR52 modulators. Compounds of the present invention may be used as GPR52 agonists. Compounds of the present invention may be useful in the treatment or prevention of diseases in which modulation of GPR52 receptors may be beneficial.

Compounds of the present invention may be used in the treatment of psychiatric disorders; neuropsychiatric disorders; neurodegenerative disorders; psychotic disorders; cognitive disorders; neurocognitive disorders; extrapyramidal disorders; movement disorders; motor disorders; hyperkinetic movement disorders; catatonia; mood disorders; depressive disorders; anxiety disorders; obsessive-compulsive disorder (OCD); autism spectrum disorders; depressive disorders; hypothalamic disorders; pituitary disorders; prolactin-related disorders; trauma- or stressor-related disorders; disruptive, impulse-control or conduct disorders; sleep-wake disorders; substance-related disorders; addictive disorders; behavioral disorders; hypofrontality; abnormalities in the tuberoinfundibular, mesolimbic, mesocortical, or nigrostriatal pathway; decreased activity in the striatum; cortical dysfunction; neurocognitive dysfunction or conditions or symptoms related thereto.

Compounds of the present invention may be used in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, anhedonia, agitation, Alzheimer's disease, Parkinson's disease, Huntington's disease, vascular dementia, Lewy body disease, frontotemporal dementia, Tourette's syndrome, hyperprolactinemia, pituitary adenoma, prolactinoma, craniopharyngioma, Cushing's disease, diabetes insipidus, non-functioning tumours, obesity, posttraumatic stress disorder (PTSD), akathisia and associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, schizotypal personality disorder, delusional disorder, brief psychotic disorder, schizophreniform disorder, schizoaffective disorder, substance- or medication-induced psychotic disorder, delusions, hallucinations, disorganized thinking, grossly disorganized or abnormal motor behavior, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorders due to another medical condition, delirium, major neurocognitive disorder, minor neurocognitive disorder, amnesia, dementia, developmental coordination disorder, stereotypic movement disorder, a post-stroke effect, dentatorubral-pallidoluysian atrophy, diminished emotional expression, avolition, alogia and asociality.

Compounds of the present invention may be used in the treatment of schizophrenia, depression, attention-deficit hyperactivity disorder (ADHD), generalised anxiety disorder, obsessive-compulsive disorder (OCD), panic disorder, bipolar disorder, addiction/impulse-control disorders, autism spectrum disorders, psychosis, neurocognitive disorder, delirium, anhedonia, agitation, Alzheimer's disease, Parkinson's disease, Huntington's disease, vascular dementia, Lewy body disease, frontotemporal dementia, Tourette's syndrome, hyperprolactinemia, obesity, and posttraumatic stress disorder (PTSD). Compounds of the present invention may be used in the treatment of schizophrenia.

Definitions

In this application, the following definitions apply, unless indicated otherwise.

The term "GPR52 modulator" as used herein refers to any compound which binds to and modulates the function of the GPR52 receptor. The term "modulator" should be interpreted to include modulation by modalities including, but not limited to, agonists, partial agonists and inverse agonists.

The term "treatment", in relation to the uses of any of the compounds described herein, including those of Formula (1) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

Terms such as "alkyl", "alkoxy", "aryl", "heteroaryl", and "cycloalkyl" are all used in their conventional sense (e.g. as defined in the IUPAC Gold Book), unless indicated otherwise. "optionally substituted" as applied to any group means that the said group may if desired be substituted with one or more substituents, which may be the same or different.

Examples of heteroatom replacements for carbon atoms include replacement of a carbon atom in a $—CH_2—CH_2—CH_2—$ chain with oxygen or sulfur to give an ether $—CH_2—O—CH_2—$ or thioether $—CH_2—S—CH_2—$, replacement of a carbon atom in a group $CH_2—C≡C—H$ with nitrogen to give a nitrile (cyano) group $CH_2—C≡N$, replacement of a carbon atom in a group $—CH_2—CH_2—CH_2—$ with C═O to give a ketone $—CH_2—C(O)—CH_2—$, replacement of a carbon atom in a group $—CH_2—CH═CH_2$ with C═O to give an aldehyde $—CH_2—C(O)H$, replacement of a carbon atom in a group $—CH_2—CH_2—CH_3$ with O to give an alcohol $—CH_2—CH_2—CH_2OH$, replacement of a carbon atom in a group $—CH_2—CH_2—CH_3$ with O to give an ether $—CH_2—O—CH_3$, replacement of a carbon atom in a group $—CH_2—CH_2—CH_3$ with S to give an thiol $—CH_2—CH_2—CH_2SH$, replacement of a carbon atom in a group $—CH_2—CH_2—CH_2—$ with S═O or $SO_2$ to give a sulfoxide $—CH_2—S(O)—CH_2—$ or sulfone $—CH_2—S(O)_2—CH_2—$, replacement of a carbon atom in a $—CH_2—CH_2—CH_2—$ chain with C(O)NH to give an amide $—CH_2—CH_2—C(O)—NH—$, replacement of a carbon atom in a $—CH_2—CH_2—CH_2—$ chain with nitrogen to give an amine $—CH_2—NH—CH_2—$, and replacement of a carbon atom in a $—CH_2—CH_2—CH_2—$ chain with C(O)O to give an ester (or carboxylic acid) $—CH_2—CH_2—C(O)—O—$. In each such replacement, at least one carbon atom of the alkyl group must remain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, there is provided a pharmaceutical composition comprising at least one compound of Formula (1) as defined above together with at least one pharmaceutically acceptable excipient.

The composition may be a tablet composition. The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the Formula (1) can be formulated in accordance with known techniques, see for example, Remington's Pharmaceutical Sciences, Mack Publishing Company, Easton, PA, USA. The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragees, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the Formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples shown in Table 1. NMR and LCMS properties are set out in Table 3. Intermediates used are listed in Table 2.

TABLE 1

| Examples |
|---|
| 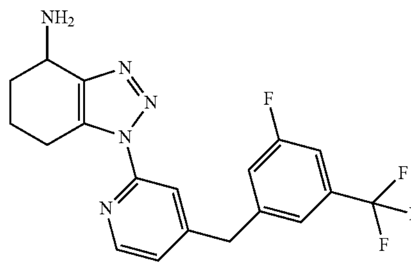<br>Example 1 |

TABLE 1-continued
| Examples |
| --- |
| 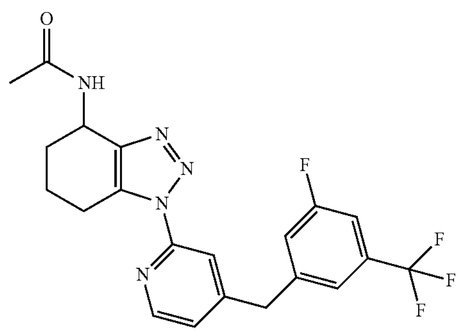 |
| Example 2 |
| 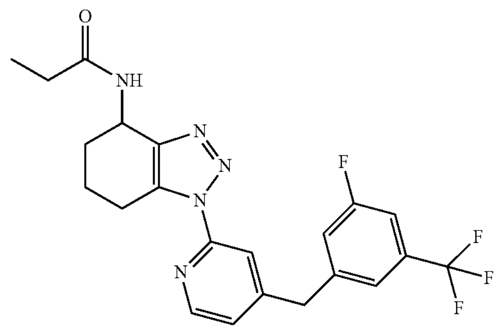 |
| Example 3 |
| 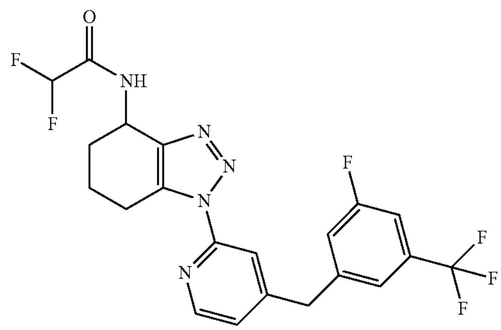 |
| Example 4 |
| 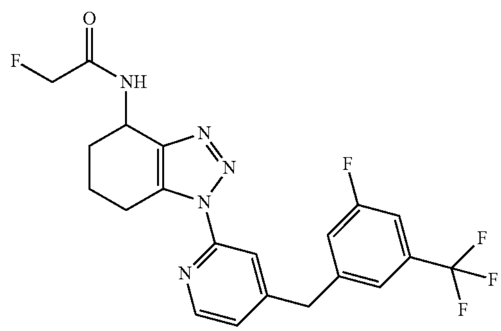 |
| Example 5 |
TABLE 1-continued
| Examples |
| --- |
| 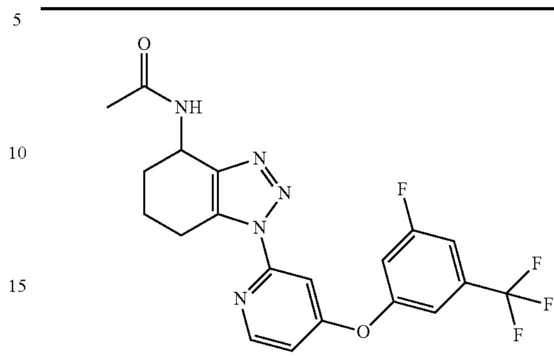 |
| Example 6 |
| 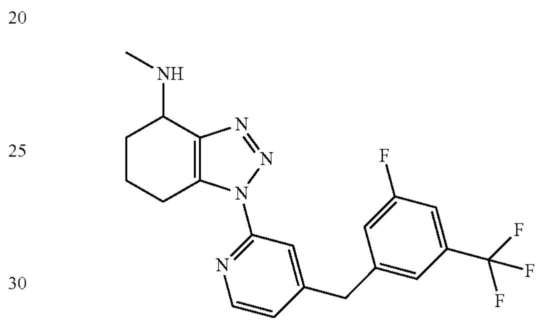 |
| Example 7 |
| 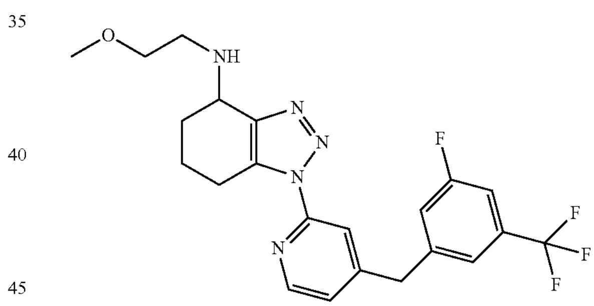 |
| Example 8 |
| 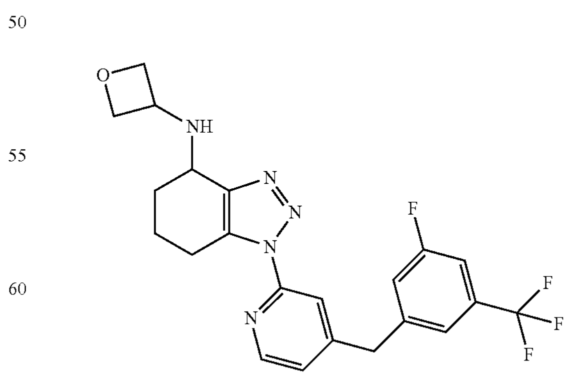 |
| Example 9 |

TABLE 1-continued
| Examples |
| --- |
| 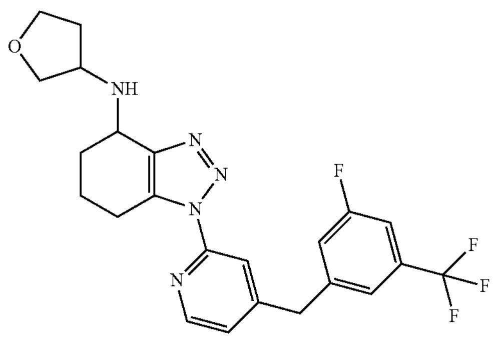<br>Example 10 |
| 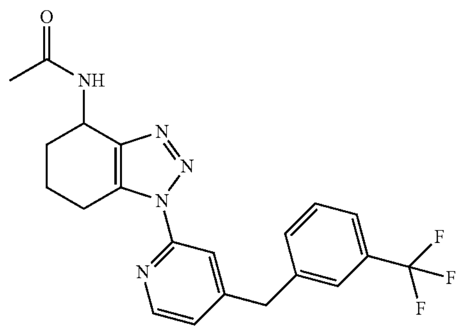<br>Example 11 |
| 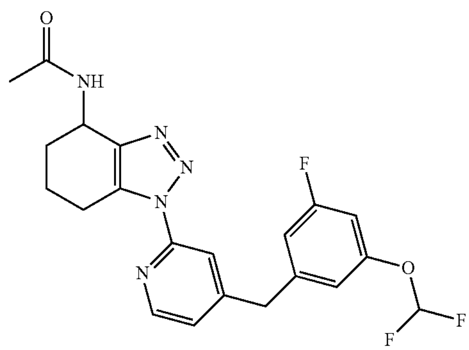<br>Example 12 |
| 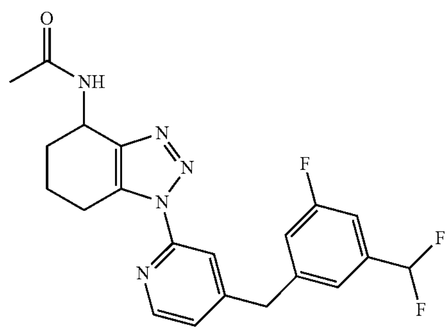<br>Example 13 |
TABLE 1-continued
| Examples |
| --- |
| 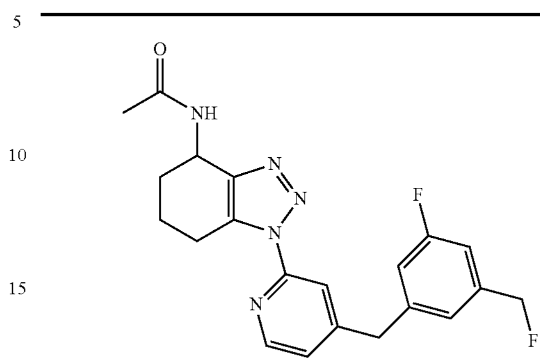<br>Example 14 |
| 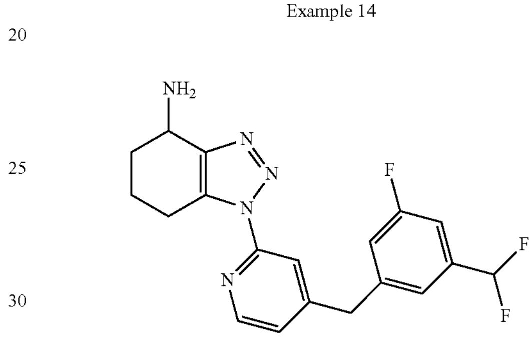<br>Example 15 |
| 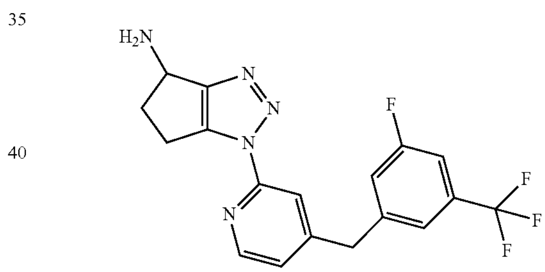<br>Example 16 |
| 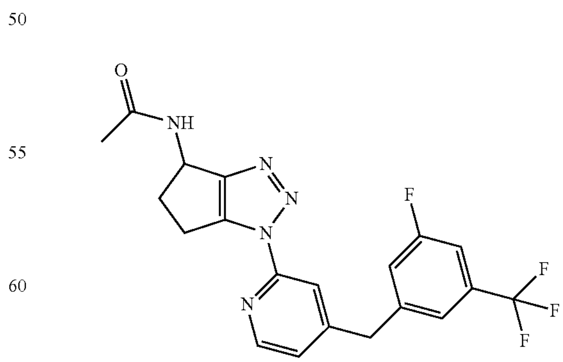<br>Example 17 |

TABLE 1-continued
| Examples |
| --- |
| 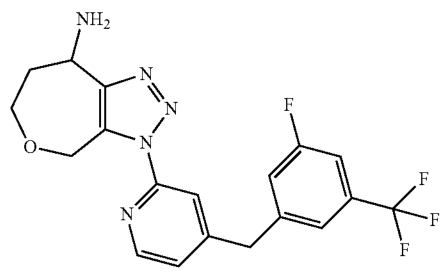<br>Example 18 |
| 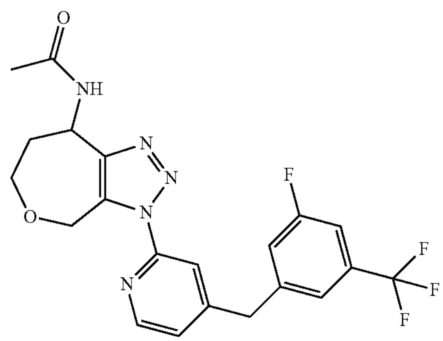<br>Example 19 |
| 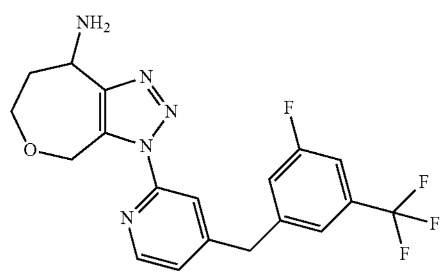<br>Example 20 |
| 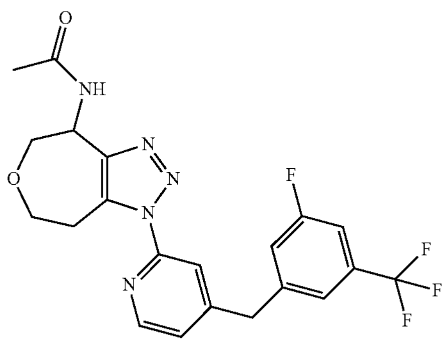<br>Example 21 |
TABLE 1-continued
| Examples |
| --- |
| 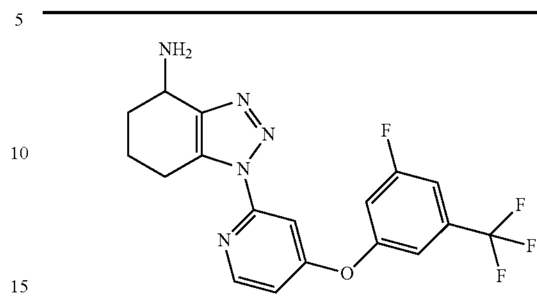<br>Example 22 |
| 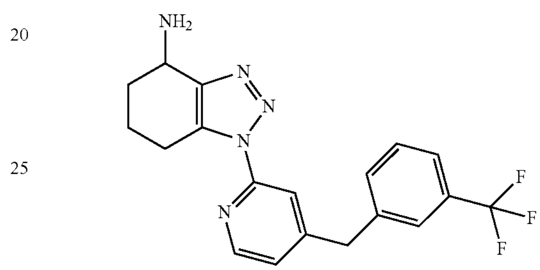<br>Example 23 |
| 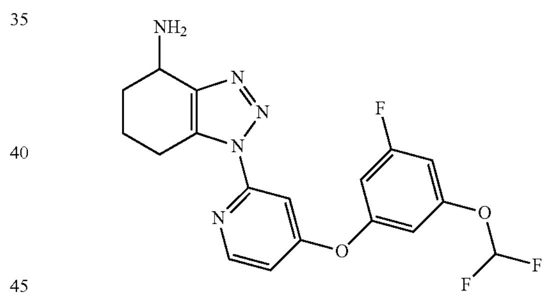<br>Example 24 |
| 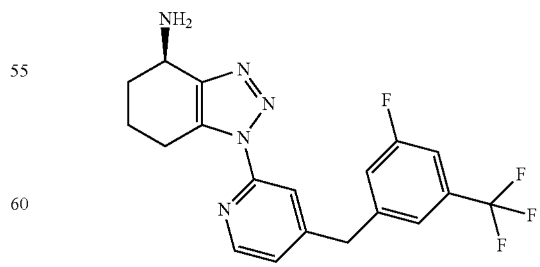<br>Example 1 - isomer 1/2 |

TABLE 1-continued

| Examples |
| --- |
| 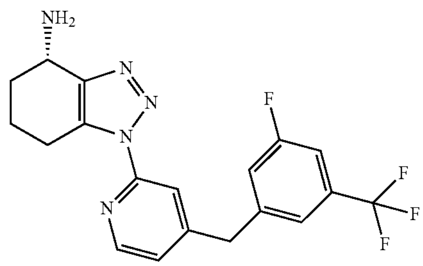 |
| Example 1 - isomer 1/2 |
| 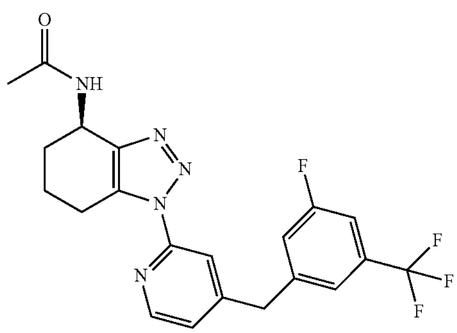 |
| Example 2 - isomer 1/2 |
| 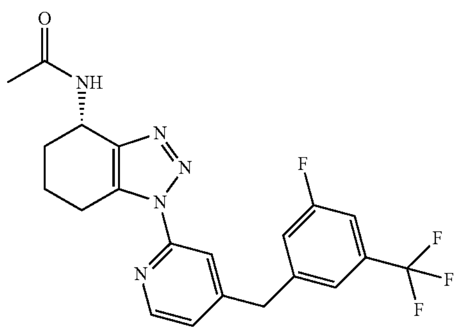 |
| Example 2 - isomer 1/2 |
| 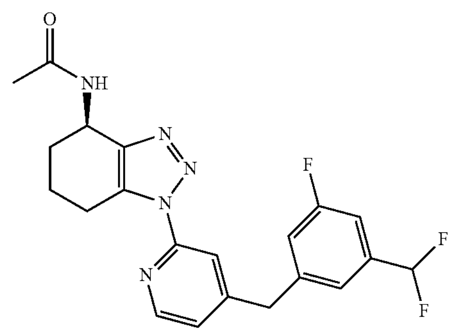 |
| Example 13 - isomer 1/2 |

TABLE 1-continued

| Examples |
| --- |
| 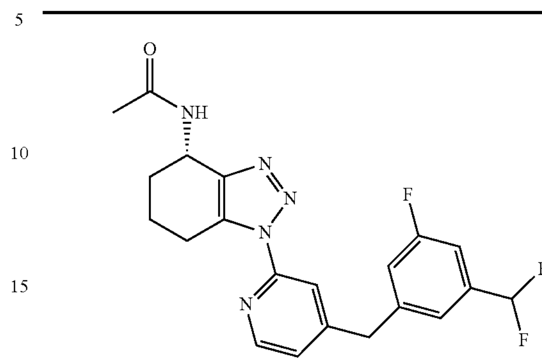 |
| Example 13 - isomer 1/2 |

Examples 1, 2 and 13 were obtained as single enantiomers following chiral separation (isomer 1 and isomer 2). Data for each individual enantiomer is provided in Table 3 and Table 4. Absolute stereochemistry of the isolated species has not been assigned however. All other Example compounds were obtained as a mixture of enantiomers and were not subjected to chiral separation. Where Example structures are drawn without indication of absolute stereochemistry, both enantiomers are included within the scope of the disclosure.

Therefore one of Example 1—isomer 1 and 2 is:

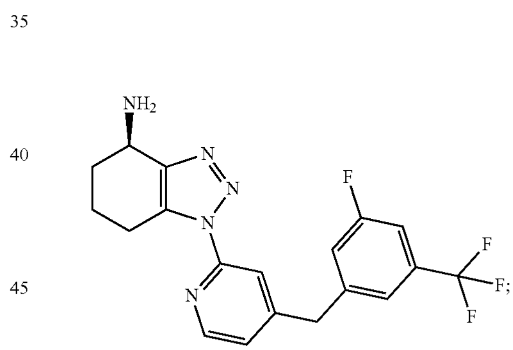

and the other is:

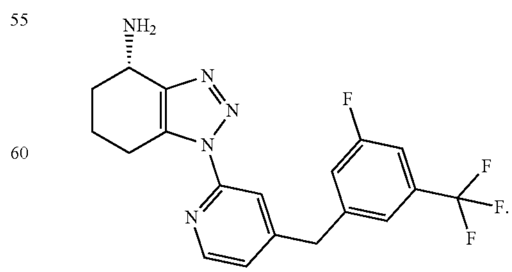

One of Example 2—isomer 1 and 2 is:

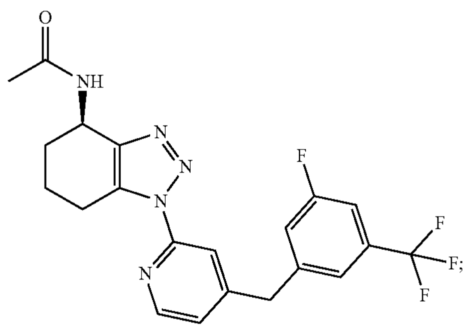 [SMILES: CC(=O)N[C@@H]1CCCc2c1nnn2-c1cc(Cc2cc(F)cc(C(F)(F)F)c2)ccn1]

and the other is:

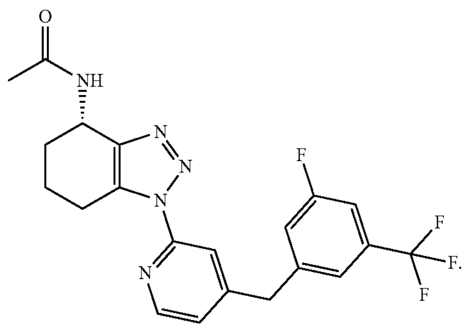 [SMILES: CC(=O)N[C@H]1CCCc2c1nnn2-c1cc(Cc2cc(F)cc(C(F)(F)F)c2)ccn1]

One of Example 13—isomer 1 and 2 is:

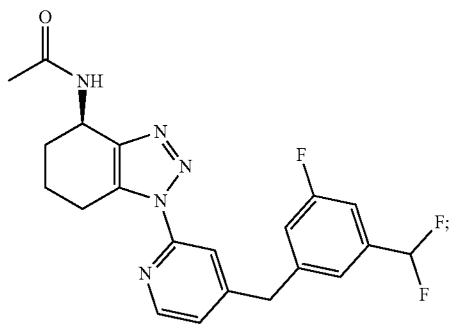 [SMILES: CC(=O)N[C@@H]1CCCc2c1nnn2-c1cc(Cc2cc(F)cc(C(F)F)c2)ccn1]

and the other is:

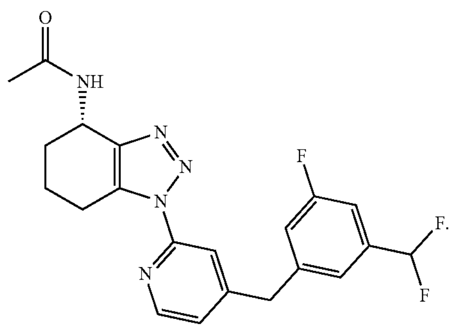 [SMILES: CC(=O)N[C@H]1CCCc2c1nnn2-c1cc(Cc2cc(F)cc(C(F)F)c2)ccn1]

Preparation of the Compounds of the Invention

Compounds of Formula (1) can be prepared in accordance with synthetic methods known to the skilled person. The invention also provides a process for the preparation of a compound as defined in Formula (1) above. Where intermediates are commercially available they are identified by their chemical abstracts service (CAS) reference number in Table 3, where not commercially available the synthesis of the intermediates using standard transformations is detailed herein. Commercial reagents were utilized without further purification.

General Procedures

Room temperature (rt) refers to approximately 20-27° C. $^1$H NMR spectra were typically recorded at 400 MHz at ambient temperature unless otherwise specified. Chemical shift values are expressed in parts per million (ppm), i.e. (b)-values. Standard abbreviations, or their combinations, are used for the multiplicity of the NMR signals, for example: s=singlet, br=broad, d=doublet, t=triplet, q=quartet, quin=quintet or p=pentet, h=heptet, dd=doublet of doublets, dt=doublet of triplets, m=multiplet. Coupling constants are listed as J values, measured in Hz. NMR and mass spectroscopy results were corrected to account for background peaks. Chromatography refers to column chromatography performed using silica or C18 silica and executed under positive pressure (flash chromatography) conditions.

LCMS Methods

LCMS experiments were carried out using electrospray conditions under the conditions below (Solvents: A1=2 mM ammonium acetate and 0.1% formic acid in $H_2O$; A2=5 mM ammonium acetate in $H_2O$; A3=2.5 L $H_2O$+2.5 mL 28% ammonia in $H_2O$ solution; A5=10 mM $NH_4HCO_3$ in $H_2O$; A6=0.2% of 28% ammonia solution in $H_2O$; A7=0.1% TFA in $H_2O$; A8=5 mM $NH_4HCO_3$ in $H_2O$; A9=10 mM ammonium acetate in $H_2O$; 1=0.1% formic acid in MeCN; B2=MeCN; B3=2.5 L MeCN+135 mL $H_2O$+2.5 mL 28% ammonia in $H_2O$ solution. LCMS data are given in the format: Mass ion, electrospray mode (positive or negative), retention time (experimental text and Table 2); Mass ion, electrospray mode (positive or negative), retention time, approximate purity (Table 3).

Method 1. Instruments: Hewlett Packard 1100 with G1315A DAD, Micromass ZQ; Column: Phenomenex Gemini-NX C18, 3 micron, 2.0×30 mm; Gradient [time (min)/solvent B3 in A3 (%)]: 0.00/2, 0.10/2, 8.40/95, 10.00/95; Injection volume 1 μL; UV detection 230 to 400 nM; Column temperature 45° C.; Flow rate 1.5 mL/min.

Method 2. Instruments: Agilent Technologies 1260 LC with Chemstation software, Diode Array Detector, Agilent 6120 Quadrupole MS with APCI and ES Source; Column: Phenomenex Gemini-NX C18, 3 micron, 2×30 mm; Gradient [time (min)/solvent B3 in A3 (%)]:0.00/2, 0.10/2, 8.40/95, 10.0/95, 10.1/2, 12.0/2; Injection volume 0.5 μL; UV detection 190-400 nm; column temperature 40° C.; Flow rate 1.5 mL/min.

Method 3. Instruments: Waters Acquity UPLC, Waters 3100 PDA Detector, SQD; Column: Acquity HSS-T3, 1.8 micron, 2.1×100 mm; Gradient [time (min)/solvent B2 in A7 (%)]: 0.0/10, 1.00/10, 2.00/15, 4.50/55, 6.00/90, 8.00/90, 9.00/10, 10.00/10; Injection volume 1 μL; Detection wavelength 214 nm; Column temperature 30° C.; Flow rate 0.3 mL per min.

Method 4. Instruments: Agilent Technologies 1260 LC with Chemstation software, Diode Array Detector, Agilent 6120 Quadrupole MS with APCI and ES Source; Column:

Phenomenex Gemini-NX C18, 3 micron, 2×30 mm; Gradient [time (min)/solvent B3 in A3 (%)]:0.00/5, 2.00/95, 2.50/95, 2.60/5, 3.00/5; Injection volume 0.5 μL; UV detection 190-400 nm; column temperature 40° C.; Flow rate 1.5 mL/min.

Method 5. Instruments: Waters Acquity UPLC, Waters 3100 PDA Detector, SQD; Column: Acquity BEH C-18, 1.7 micron, 2.1×100 mm; Gradient [time (min)/solvent B2 in A2 (%)]: 0.00/2, 2.00/2, 7.00/50, 8.50/80, 9.50/2, 10.0/2; Injection volume 1 μL; Detection wavelength 214 nm; Column temperature 30° C.; Flow rate 0.3 mL per min.

Method 6. Instruments: Agilent Technologies 1290 Infinity II Series LC, 6125 Quadrupole MSD SL; Column: Zorbax XDB C18, 5 micron; Gradient [time (min)/solvent B2 in A4 (%)]:0.00/5, 2.50/95, 4.00/95, 4.50/5, 6.00/5; Injection volume 1 μL; UV detection 210-400 nm; Column temperature 25° C.; Flow rate 1.5 mL/min.

Method 7. Instruments: Agilent Technologies 1290 Infinity II Series LC, 6125 Quadrupole MSD SL; Column: Waters XBridgeC8 3.5 micron, 4.6×50 mm; Gradient [time (min)/solvent 1 in A1 (%)]:0.0/5, 2.5/95, 4.0/95, 4.5/5, 6.0/5; Injection volume 1 μL; UV detection 210 to 400 nM; Column temperature 25° C.; 1.5 mL/min.

Method 8. Instruments: Agilent Technologies 1290 Infinity II Series LC, 6125 Quadrupole MSD SL; Column: Zorbax extend C18, 5 micron, 4.6×50 mm; Gradient [time (min)/solvent B2 in A9 (%)]:0.0/10, 4.0/95, 5.0/95, 5.5/5, 6.0/5; Injection volume 1 μL; UV detection 210-400 nm; Column temperature 25° C.; Flow rate 1.2 mL/min Method 9. Instruments: Waters Acquity UPLC, Waters 3100 PDA Detector, SQD; Column: Acquity BEH C-18, 1.7 micron, 2.1×100 mm; Gradient [time (min)/solvent B2 in A2 (%)]: 0.00/5, 0.25/5, 1.50/35, 2.50/95, 3.20/95, 3.60/5, 4.00/5; Injection volume 1 μL; Detection wavelength 214 nm; Column temperature 35° C.; Flow rate 0.6 mL per min to 3.20 min then 0.8 mL per min.

Method 10. Instruments: Waters Acquity H Class, Waters PDA Detector, SQD; Column: Acquity BEH C-18, 1.7 micron, 2.1×50 mm; Gradient [time (min)/solvent 1 in A1 (%)]: 0.00/5, 0.60/70, 0.8/90, 1.1/100, 1.70/100, 1.71/5, 2.00/5; Injection volume 1 μL; Detection wavelength 200-400 nm; Column temperature RT; Flow rate 0.55 mL per min to 0.60 min then 0.60 mL per min to 0.80 min then 0.65 mL per min to 1.71 min then 0.55 mL per min.

GCMS Methods

GCMS data are given in the format: Mass ion, electrospray mode (positive or negative), retention time.

Method 1. Instrument: Agilent GCMS 7890B; Column: HP-5 ms UI (30 m×250 μm×0.25 μm); Inlet temp: 250° C.; Spit ratio: 75:1; Oven temp: 50° C., hold time 3 min; Ramp 1: 40° C./min to 300° C., hold time 2 min; Detector temperature: 310° C.; Column flow: 2 mL/min; Air flow: 300 mL/min; $H_2$ flow: 40 mL/min; Make up flow (He): 25 mL/min; Source temp: 230° C.

Method 2. Instrument: Agilent GCMS 7890B; Column: HP-5 ms UI (30 m×250 μm×0.25 μm); Inlet temp: 250° C.; Split ratio: 75:1; Oven temp: 120° C., hold time 1 min; Ramp 1: 40° C./min to 300° C., hold time 4 min; Detector temperature: 310° C.; Column flow: 2 mL/min; Air flow: 300 mL/min; $H_2$ flow: 40 mL/min; Make up flow (He): 25 mL/min; Source temp: 230° C.

MS Methods

Method 1. Data acquired on either a Waters QDA or Waters SQD instrument after a 4-6 minute run through a UPLC column using buffer.

Prep HPLC Methods

See LCMS methods section for solvent conditions.

Method 1. Instruments: Waters 2767 Auto purification; Column: X-Bridge Shield C18 10 micron 19×250 mm; Gradient 20 min, solvent B2 in A2 (%) varies on individual run basis (see exemplified procedures for details).

Method 2. Instruments: Gilson Semi Preparative HPLC System—321 Pump/171 Diode Array Detector/GX-271 Liquid Handler; Column: Phenomenex Gemini-NX C18 5 micron 30×100 mm; Gradient 12.5 min, solvent B2 in A6 (%) varies on individual run basis (see exemplified procedures for details).

Method 3. Instruments: Waters 2767 Auto purification; Column: Xtimate hexyl phenyl 10 micron 19×250 mm; Gradient 18 min, solvent B2 in A7 (%) varies on individual run basis (see exemplified procedures for details).

Method 4. Instruments: Agilent Technologies 1260 Infinity II Series LC/6125 Quadrupole MSD; Column: Waters XBridge C8 5 micron 19×150 mm; Gradient [time (min)/solvent B2 in A5 (%)]:0.0/10, 15/95, 18/95, 19/10, 21/10.

Chiral SFC Methods

Method 1. Instruments: Sepiatec Prep SFC 100 with Prep SFC 100 control software and UV/Vis detector; Column: Lux C1 5 micron, 21.2×250 mm; Co-solvent EtOH; Column temperature 40° C.; 50 mL/min.

Method 2. Instruments: Sepiatec Prep SFC 100 with Prep SFC 100 control software and UV/Vis detector; Column: Lux A1 5 micron, 21.2×250 mm; Co-solvent 0.2% $NH_3$ in IPA; Column temperature 40° C.; 50 mL/min.

Method 3. Instruments: Waters Acquity UPC2 with Masslynx software, PDA detector and a QDa mass detector; Column: Lux A1 3 micron, 2×50 mm; Co-solvent EtOH; Column temperature 45° C.; 1.5 mL/min.

Method 4. Instruments: Waters Acquity UPC2 with Masslynx software, PDA detector and a QDa mass detector; Column: Lux A1 3 micron, 2×50 mm; Co-solvent IPA; Column temperature 45° C.; 1.5 mL/min.

Method 5. Instruments: Sepiatec Prep SFC 100 with Prep SFC 100 control software and UV/Vis detector; Column: Lux C1 5 micron, 21.2×250 mm; Co-solvent 0.2% $NH_3$ in MeOH; Column temperature 40° C.; 50 mL/min.

Method 6. Instruments: Waters Acquity UPC2 with Masslynx software, PDA detector and a QDa mass detector; Column: Lux C1 3 micron, 2×50 mm; Co-solvent 0.1% $NH_3$ in MeOH; Column temperature 45° C.; 1.5 mL/min.

Abbreviations aq=aqueous
Boc=tert-butoxycarbonyl
DAST=(diethylamino)sulfur trifluoride
DavePhos=2-dicyclohexylphosphino-2'-(N,N-dimethylamino)biphenyl
dba=dibenzylideneacetone
DCM=dichloromethane
Dess-Martin=1,1,1-tris(acetyloxy)-1,1-dihydro-1,2-benziodoxol-3-(1H)-one
DIPEA=N,N-diisopropylethylamine
DMSO=dimethylsulfoxide
dppf=1,1'-ferrocenediyl-bis(diphenylphosphine)
ES=electrospray
EtOAc=ethyl acetate
EtOH=ethanol
h=hour(s)
HATU=1-[bis(dimethylamino)methylene]-1H-1,2,3-triazolo[4,5-b]pyridinium 3-oxid hexafluorophosphate
IPA=i-propyl alcohol
L=litre
LC=liquid chromatography LCMS=liquid chromatography mass spectrometry $LiAlH_4$=lithium aluminum hydride MeCN=acetonitrile MeOH=methanol min=minute(s)

MS=mass spectrometry

NMP=1-methyl-2-pyrrolidinone

NMR=nuclear magnetic resonance

Pet-ether=petroleum ether pin=pinacolato

RT=room temperature

SPhos=2-dicyclohexylphosphino-2',6'-dimethoxybiphenyl

TEA=triethylamine

TFA=trifluoroacetic acid

THF=tetrahydrofuran

Ts=para-toluenesulfonyl

Prefixes n-, s-, i-, t- and tert- have their usual meanings: normal, secondary, iso, and tertiary.

Synthesis of Intermediates

Intermediate 1, 1-(4-(3-fluoro-5-(trifluoromethyl)benzyl)pyridin-2-yl)-1,5,6,7-tetrahydro-4H-benzo[d][1,2,3]triazol-4-one

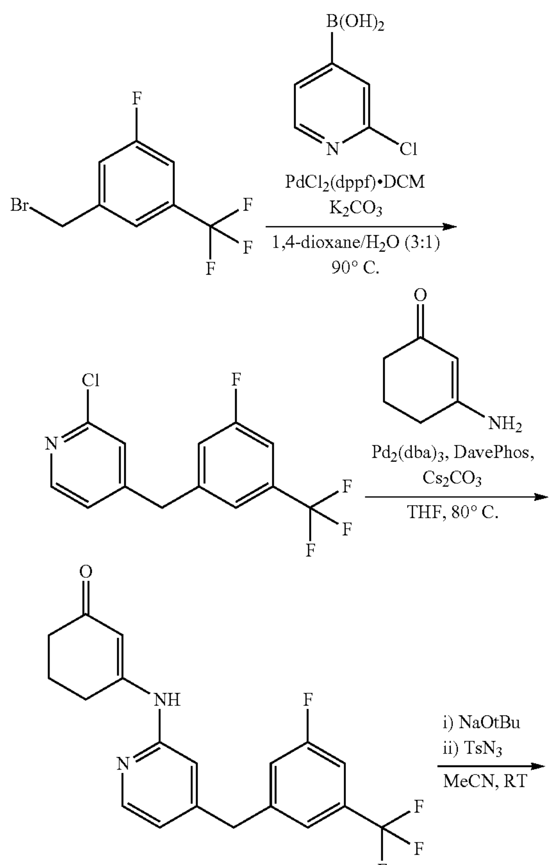

-continued

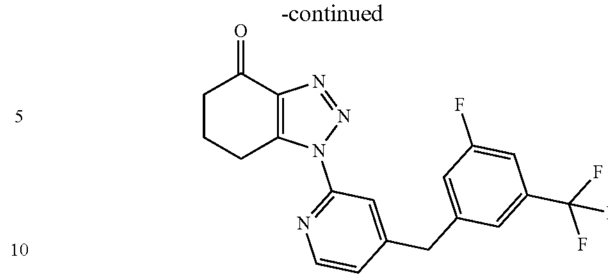

Step 1. (2-Chloropyridin-4-yl)boronic acid (24.5 g, 156 mmol) was added to a solution of 1-(bromomethyl)-3-(trifluoromethyl)benzene (40.0 g, 156 mmol) in 1,4-dioxane (450 mL)/water (150 mL) and the reaction mixture purged with $N_2$ for 10 min. Potassium carbonate (64.5 g, 467 mmol) and $PdCl_2$(dppf).DCM (6.35 g, 7.70 mmol) were added and the resultant reaction mixture heated at 90° C. for 4 h. The reaction mixture was filtered through Celite which was then rinsed with EtOAc (400 mL). The filtrate was washed with water (400 mL) and the organic layer separated. The aqueous layer was extracted with EtOAc (3×200 mL), the combined organic layers dried ($Na_2SO_4$) and the solvent removed in vacuo. The residue was purified by gradient flash column chromatography eluting with 0-10% EtOAc in hexane to afford 2-chloro-4-(3-fluoro-5-(trifluoromethyl)benzyl)pyridine as a colourless oil (34.5 g, 77%).

LCMS (Method 10): m/z 290.3, 292.3 (ES+), at 1.39 min.

$^1$H NMR: (400 MHz, DMSO-$d_6$) δ: 8.34 (d, J=5.2 Hz, 1H), 7.63-7.53 (m, 4H), 7.37 (d, J=4.8 Hz, 1H), 4.13 (s, 2H).

Step 2. 2-Chloro-4-(3-fluoro-5-(trifluoromethyl)benzyl)pyridine (25.0 g, 86.3 mmol) was added to a stirred solution of 3-aminocyclohex-2-en-1-one (11.5 g, 104 mmol) in THF (250 mL). The reaction mixture was purged with $N_2$ for 10 min and $Pd_2(dba)_3$ (3.95 g, 4.30 mmol), DavePhos (3.39 g, 8.63 mmol) and $Cs_2CO_3$ (70.3 g, 216 mmol) were sequentially added to the reaction mixture. The reaction mixture was heated at 80° C. for 8 h and then filtered through Celite. The filtrate was partitioned between EtOAc (500 mL) and water (400 mL). The organic layer was separated and the solvent was removed in vacuo. The residue was purified by gradient flash column chromatography eluting with 0-100% EtOAc in hexane to afford 3-((4-(3-fluoro-5-(trifluoromethyl)benzyl)pyridin-2-yl)amino)cyclohex-2-en-1-one as a brown solid (13.5 g, 43%).

LCMS (Method 10): m/z 365.3 (ES+), at 1.26 min.

$^1$H NMR: (400 MHz, $CDCl_3$) δ: 8.27 (d, J=5.2 Hz, 1H), 7.36-7.22 (m, 2H), 7.09 (d, J=9.2 Hz, 1H), 6.94 (d, J=10.2 Hz, 2H), 6.79 (d, J=5.2 Hz, 1H), 6.39 (s, 1H), 4.04 (s, 2H), 2.60 (t, J=6.2 Hz, 2H), 2.45 (t, J=6.5 Hz, 2H), 2.11 (dd, J=13.0, 6.6 Hz, 2H).

Step 3. 3-((4-(3-fluoro-5-(trifluoromethyl)benzyl)pyridin-2-yl)amino)cyclohex-2-en-1-one (10.0 g, 27.5 mmol) was added to a suspension of sodium tert-butoxide (3.96 g, 41.2 mmol) in MeCN (350 mL) at RT. A solution of tosyl azide (5.42 g, 36.6 mmol) in MeCN (50 mL) was added dropwise. The reaction mixture was stirred for 12 h at RT and water (600 mL) was added. The aqueous layer was extracted with EtOAc (3×600 mL) and the combined organic layers were dried ($Na_2SO_4$) and the solvent removed in vacuo. The residue was purified by gradient flash column chromatography eluting with 0-50% EtOAc in hexane to afford 1-(4-(3-fluoro-5-(trifluoromethyl)benzyl)pyridin-2-yl)-1,5,6,7-tetrahydro-4H-benzo[d][1,2,3]triazol-4-one as an off white solid (5.6 g, 52%). Data in table 2.

Intermediate 2, 2-fluoro-4-(3-(trifluoromethyl)benzyl)pyridine

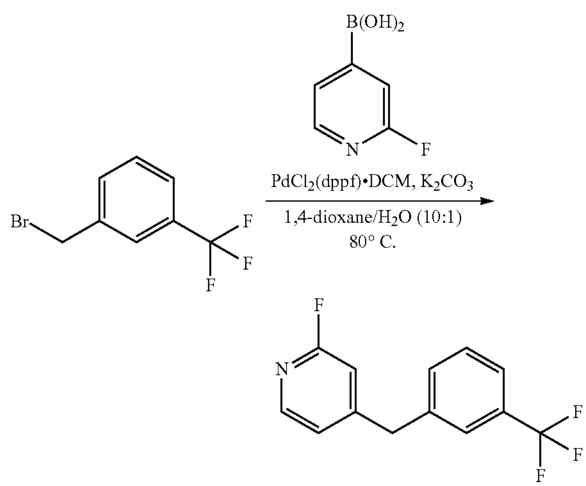

1-(Bromomethyl)-3-(trifluoromethyl)benzene (0.14 mL, 0.88 mmol) was added to a suspension of 2-fluoropyridine-4-boronic acid (150 mg, 1.06 mmol), potassium carbonate (146 mg, 1.06 mmol) and $PdCl_2$(dppf).DCM (129 mg, 0.18 mmol) in 1,4-dioxane (4 mL)/water (0.4 mL) and the resultant reaction mixture heated at 80° C. for 2 h. The reaction mixture was partitioned between water (6 mL) and EtOAc (6 mL) and the organic layer removed. The aqueous layer was extracted with EtOAc (2×6 mL), the combined organic layers dried (phase separator) and the solvent removed in vacuo. The residue was purified by gradient flash column chromatography eluting with 0-50% EtOAc in i-hexane to afford 2-fluoro-4-(3-(trifluoromethyl)benzyl) pyridine as a yellow liquid (167 mg, 74%). Data in table 2.

Intermediate 3. 1,5,6,7-tetrahydro-4H-benzo[d][1,2,3]triazol-4-one

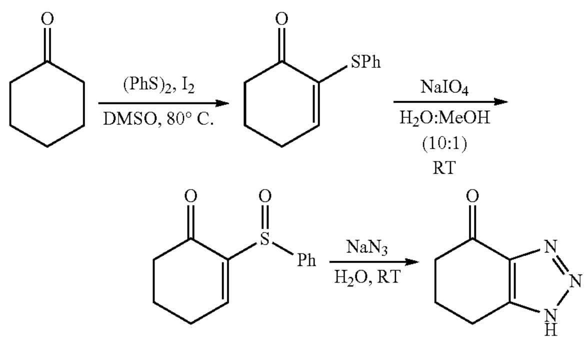

Step 1. Iodine (0.260 g, 1 mmol) was added to a stirred mixture of cyclohexanone (2 g, 20 mmol) and 1,2-diphenyldisulfane (1.7 g, 80 mmol) in DMSO (12 mL) and the reaction mixture was heated at 80° C. for 12 h. The reaction was quenched by the addition of water (100 mL) and the aqueous layer was extracted with EtOAc (3×100 mL). The organic layers were combined, dried ($Na_2SO_4$) and the solvent removed in vacuo to afford 2-(phenylthio) cyclohex-2-en-1-one as a yellow liquid (4.5 g crude). The crude product was used in the next step without further purification.

MS (Method 1): m/z 205 (ES+).

Step 2. Sodium periodate (9.39 g, 40 mmol) was added to a stirred solution of 2-(phenylthio)cyclohex-2-en-1-one (4.5 g, 22 mmol) in MeOH (1.2 mL) and $H_2O$ (12 mL) and the reaction mixture was stirred at room temperature for 16 h. The reaction was quenched by the addition of water (100 mL) and the aqueous layer was extracted with EtOAc (3×100 mL). The organic layers were combined, dried ($Na_2SO_4$) and the solvent removed in vacuo. The residue was purified by gradient flash column chromatography eluting with 30-35% EtOAc in hexane to afford 2-(phenylsulfinyl)cyclohex-2-en-1-one as an orange gum (2.1 g, 43%).

MS (Method 1): m/z 221 (ES+).

Step 3. Sodium azide (324 mg, 4 mmol) was added to a stirred solution of 2-(phenylsulfinyl)cyclohex-2-en-1-one (1 g, 4 mmol) in $H_2O$ (17 mL) and the reaction mixture was stirred at room temperature for 16 h. The reaction mixture was acidified to pH 2 using 1 N HCl (19 mL) and water (100 mL) was added. The aqueous layer was extracted with EtOAc (3×100 mL). The organic layers were combined, dried ($Na_2SO_4$) and the solvent removed in vacuo to give 1,5,6,7-tetrahydro-4H-benzo[d][1,2,3]triazol-4-one as an off white solid (220 mg, 35%). Data in table 2.

Intermediate 4, tert-butyl (1-(4-bromopyridin-2-yl)-4,5,6,7-tetrahydro-1H-benzo[d][1,2,3]triazol-4-yl) carbamate

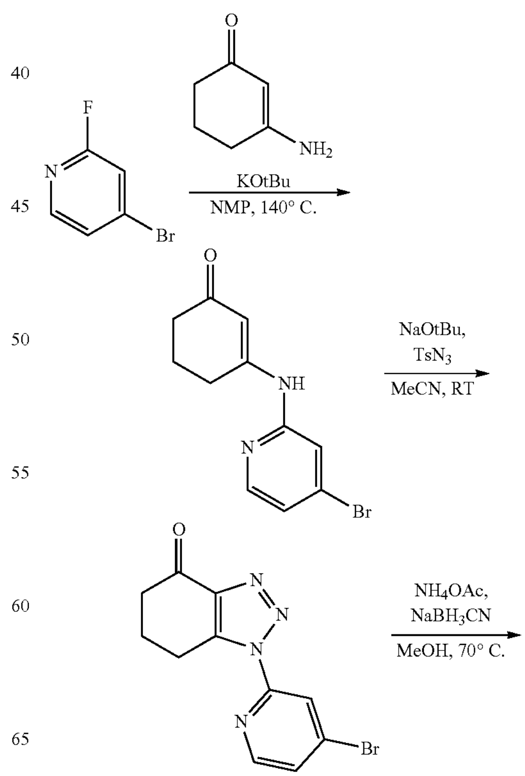

-continued

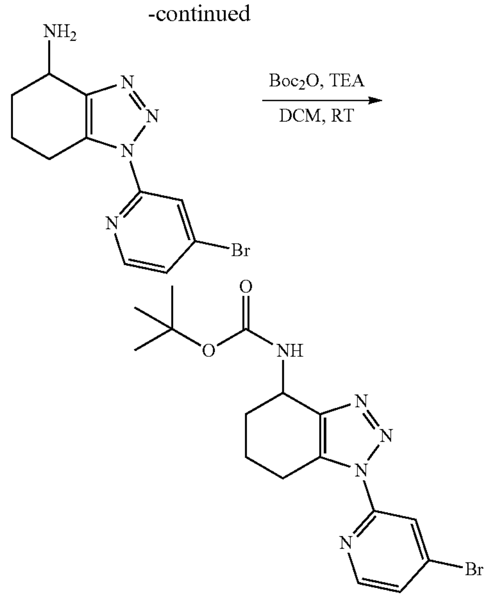

Step 1. KOtBu (47.7 g, 426.0 mmol) was added to a stirred solution of 4-bromo-2-fluoropyridine (25 g, 142 mmol) and 3-aminocyclohex-2-en-1-one (23.6 g, 213 mmol) in NMP (300 mL) and the resultant reaction mixture was heated at 140° C. for 12 h. The reaction mixture was partitioned between water (4×500 mL) and EtOAc (2×200 mL). The combined organic layers were washed with brine (300 mL), dried ($Na_2SO_4$) and the solvent removed in vacuo to afford 3-((4-bromopyridin-2-yl)amino)cyclohex-2-en-1-one (5.1 g, 13%) as an off-white solid.

LCMS (Method 6): m/z 267.0 (ES+), at 1.38 min.

$^1$H NMR: (400 MHz, DMSO-d$_6$) δ: 9.33 (s, 1H), 8.19 (d, J=5.6 Hz, 1H), 7.25-7.20 (m, 2H), 6.86 (s, 1H), 2.70-2.50 (m, 2H), 2.34-2.19 (m, 2H), 2.00-1.58 (m, 2H).

Step 2. $TsN_3$ (1.7 mL, 11.23 mmol) and NaOtBu (2.15 mg, 22.4 mmol) were added to a stirred solution of 3-((4-bromopyridin-2-yl)amino)cyclohex-2-en-1-one (2 g, 7.49 mmol) in MeCN (40 mL) and the resultant reaction mixture was stirred at RT for 1 h. The reaction mixture was partitioned between water (100 mL) and EtOAc (200 mL). The organic layer was separated, washed with brine (100 mL), dried ($Na_2SO_4$) and the solvent removed in vacuo. The residue was purified by gradient flash column chromatography eluting with 0-25% EtOAc in pet-ether to afford 1-(4-bromopyridin-2-yl)-1,5,6,7-tetrahydro-4H-benzo[d][1,2,3]triazol-4-one (1.1 g, 50%) as a yellow solid.

LCMS (Method 6): m/z 293.0 (ES+), at 1.74 min.

$^1$H NMR: (400 MHz, DMSO-d$_6$) δ: 8.58-8.56 (m, 1H), 8.35 (d, J=1.2 Hz, 1H), 7.92-7.90 (m, 1H), 3.37-3.33 (m, 2H), 2.68-2.58 (m, 2H), 2.19-2.12 (m, 2H).

Step 3. $NH_4OAc$ (2.62 g, 34.1 mmol) and molecular sieves (2.62 g) were added to a stirred solution of 1-(4-bromopyridin-2-yl)-1,5,6,7-tetrahydro-4H-benzo[d][1,2,3]triazol-4-one (1 g, 3.41 mmol) in MeOH (50 mL), followed by the addition of $NaBH_3CN$ (0.641 g, 10.2 mmol) and the resultant reaction mixture was heated at 70° C. for 16 h. The reaction mixture was filtered through Celite and which was rinsed with EtOAc (50 mL). The filtrate was partitioned between water (50 mL) and EtOAc (50 mL). The organic layer was separated, washed with brine (50 mL), dried ($Na_2SO_4$) and the solvent removed in vacuo to afford 1-(4-bromopyridin-2-yl)-4,5,6,7-tetrahydro-1H-benzo[d][1,2,3]triazol-4-amine (1.01 g, crude) as a brown gum. The crude material was used in the next step without further purification.

LCMS (Method 6): m/z 294.0 (ES+), at 1.03 min.

$^1$H NMR: (400 MHz, DMSO-d$_6$) δ: 8.51-8.49 (m, 1H), 8.26-8.23 (m, 1H), 7.82-7.80 (m, 1H), 4.05 (t, J=5.6 Hz, 1H), 3.10-2.95 (m, 2H), 2.20-1.89 (m, 6H).

Step 4. TEA (1.42 mL, 10.23 mmol) was added to a stirred solution of 1-(4-bromopyridin-2-yl)-4,5,6,7-tetrahydro-1H-benzo[d][1,2,3]triazol-4-amine (1 g, 3.41 mmol) in DCM (30 mL) followed by the addition of $(Boc)_2O$ (1.48 mL, 6.82 mmol) and the resultant reaction mixture was stirred at RT for 16 h. The reaction mixture was partitioned between water (50 mL) and DCM (50 mL). The organic layer was separated, dried ($Na_2SO_4$) and the solvent removed in vacuo. The residue was purified by gradient flash column chromatography eluting with 0-30% EtOAc in pet-ether to afford tert-butyl (1-(4-bromopyridin-2-yl)-4,5,6,7-tetrahydro-1H-benzo[d][1,2,3]triazol-4-yl)carbamate (750 mg, 56%) as a white solid. Data in table 2.

Intermediate 5, 1-(chloromethyl)-3-(difluoromethyl)-5-fluorobenzene

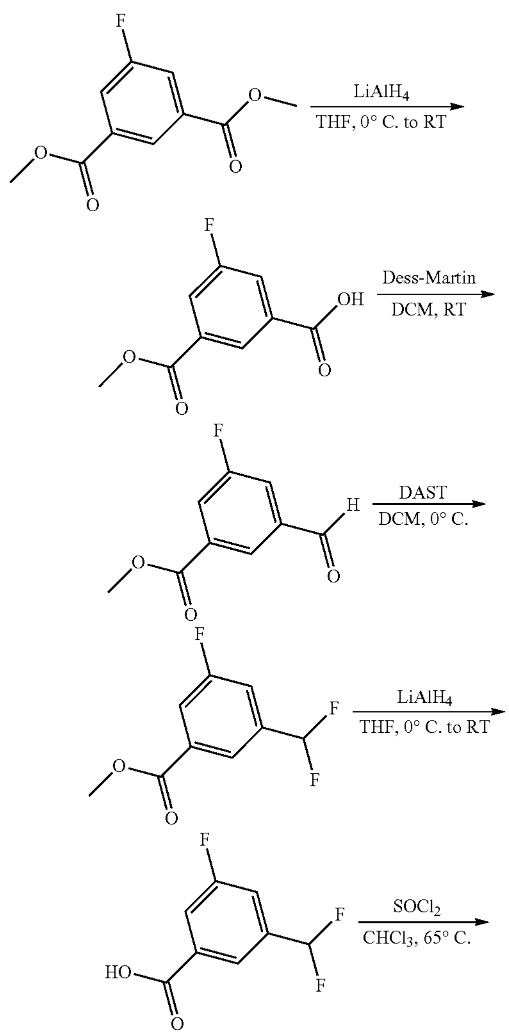

-continued

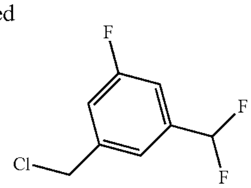

Step 1. $LiAlH_4$ (1.0 M in THF, 7.0 mL, 7.0 mmol) was added to a stirred solution of dimethyl 5-fluoroisophthalate (3 g, 14.1 mmol) in THF (10 mL), at 0° C. and the resultant reaction mixture was stirred at RT for 3 h. The reaction mixture was neutralized with 1.5 N HCl (50 mL) up to pH ~7, and the reaction mixture was partitioned between water (100 mL) and EtOAc (50 mL). The organic layer was separated, dried ($Na_2SO_4$) and the solvent removed in vacuo to afford methyl 3-fluoro-5-(hydroxymethyl)benzoate (1.12 g. 43%) as a colourless liquid.

GCMS (Method 1): m/z 184.0 (ES+), at 7.34 min.

$^1H$ NMR: (400 MHz, DMSO-$d_6$) δ: 7.79 (s, 1H), 7.55 (d, J=12.8 Hz, 1H), 7.43 (d, J=12.8 Hz, 1H), 5.49 (t, J=7.6 Hz, 1H), 4.58 (d, J=7.6 Hz, 2H), 3.87 (d, J=2.4 Hz, 3H).

Step 2. Dess-Martin periodinane (2.3 g, 5.54 mmol) was added to a stirred solution of methyl 3-fluoro-5-(hydroxymethyl)benzoate (510 mg, 2.77 mmol) in DCM (10 mL) and the resultant reaction mixture was stirred at RT for 2 h. The reaction mixture was filtered and the filtrate was concentrated in vacuo. The residue was purified by gradient flash column chromatography eluting with 0-30% EtOAc in hexane to afford methyl 3-fluoro-5-formylbenzoate (410 mg, 81%) as a white solid.

GCMS (Method 1): m/z 182.0 (ES+), at 6.76 min.

$^1H$ NMR: (400 MHz, DMSO-$d_6$) δ: 10.08 (d, J=2.4 Hz, 1H), 8.33 (d, J=1.6 Hz, 1H), 8.05-8.04 (m, 2H), 3.92 (s, 3H).

Step 3. DAST (0.44 mL, 3.37 mmol) was added to a stirred solution of methyl 3-fluoro-5-formylbenzoate (410 mg, 2.25 mmol) at 0° C. and the resultant reaction mixture was stirred at RT for 2 h. The reaction mixture was neutralized with 10% aq $NaHCO_3$ (20 mL) up to pH ~7, and reaction mixture was partitioned between water (100 mL) and DCM (50 mL). The organic layer was separated, dried ($Na_2SO_4$) and the solvent removed in vacuo. The residue was purified by gradient flash column chromatography eluting with 0-30% EtOAc in hexane to afford methyl 3-(difluoromethyl)-5-fluorobenzoate (400 mg, 87%) as a colourless liquid.

GCMS (Method 2): m/z 204.0 (ES+), at 2.36 min.

$^1H$ NMR: (400 MHz, DMSO-$d_6$) δ: 7.99 (s, 1H), 7.89 (d, J=11.2 Hz, 1H), 7.80 (d, J=11.2 Hz, 1H), 7.35-6.98 (m, 1H), 3.91 (s, 3H).

Step 4. $LiAlH_4$ (2.0 M in THF, 0.45 mL, 0.90 mmol) was added to a stirred solution of methyl 3-(difluoromethyl)-5-fluorobenzoate (390 mg, 1.81 mmol) in THF (10 mL) at 0° C. and the resultant reaction mixture was stirred at RT for 1 h. The reaction mixture was neutralized with 1.5 N HCl (50 mL) up to pH ~7 and then partitioned between water (100 mL) and EtOAc (50 mL). The organic layer was separated, dried ($Na_2SO_4$) and the solvent removed in vacuo to afford (3-(difluoromethyl)-5-fluorophenyl)methanol (230 mg, 72%) as a colourless liquid.

GCMS (Method 2): m/z 176.0 (ES+), at 6.36 min.

$^1H$ NMR: (400 MHz, DMSO-$d_6$) δ: 7.39 (s, 1H), 7.32-7.29 (m, 3H), 5.46 (d, J=6.4 Hz, 1H), 4.57 (t, J=6.4 Hz, 2H).

Step 5. Thionyl chloride (3 mL, 43.2 mmol) was added to a stirred solution of (3-(difluoromethyl)-5-fluorophenyl) methanol (170 mg, 0.96 mmol) in chloroform (10 mL) at RT and the resultant reaction mixture was heated at 65° C. for 12 h. The reaction mixture was neutralized with 10% aq $NaHCO_3$ (20 mL) up to pH ~7, then partitioned between water (50 mL) and EtOAc (50 mL). The organic layer was separated, dried ($Na_2SO_4$) and the solvent removed in vacuo to afford 1-(chloromethyl)-3-(difluoromethyl)-5-fluorobenzene (170 mg, crude) as a colourless liquid. The crude material was used in the next step without further purification. Data in table 2.

Intermediate 6, 1-(chloromethyl)-3-fluoro-5-(fluoromethyl)benzene

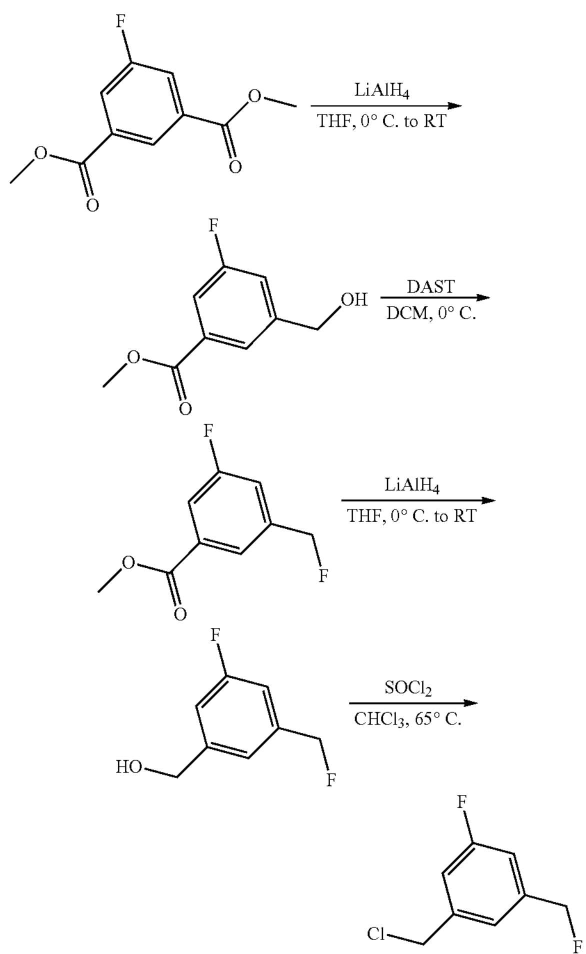

The title compound (220 mg, 19%) was prepared in four steps from dimethyl 5-fluoroisophthalate (2.68 g, 12.6 mmol) using the methods of Intermediate 5, steps 1, 3, 4 and 5. After completion of step 4, the title compound was isolated as a colourless oil by partitioning between DCM (50 mL) and 10% aq $NaHCO_3$ (25 mL). The organic layer was separated, dried ($Na_2SO_4$) and the solvent removed in vacuo. Data in table 2.

Synthesis of Examples

Typical procedures for the preparation of examples, as exemplified by the preparation of the below examples in Procedures 1-9.

Procedure 1

Example 1, 1-(4-(3-fluoro-5-(trifluoromethyl)benzyl)pyridin-2-yl)-4,5,6,7-tetrahydro-1H-benzo[d][1,2,3]triazol-4-amine

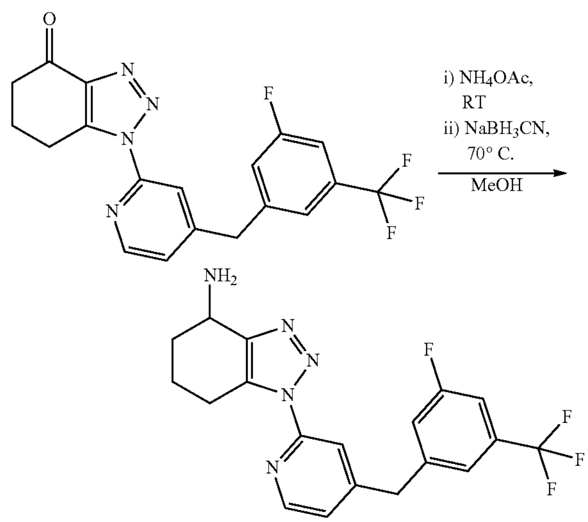

Ammonium acetate (1.18 g, 15.4 mmol) was added to a stirred solution of 1-(4-(3-fluoro-5-(trifluoromethyl)benzyl)pyridin-2-yl)-1,5,6,7-tetrahydro-4H-benzo[d][1,2,3]triazol-4-one (Intermediate 1, 400 mg, 1.02 mmol) in MeOH (10 mL) and the reaction mixture was stirred at RT for 16 h. $NaBH_3CN$ (193 mg, 3.07 mmol) was then added and the reaction mixture was heated at 70° C. for 16 h. The solvent was removed in vacuo and the residue was quenched with aq $NaHCO_3$ solution (30 mL). The aqueous layer was extracted with EtOAc (3×30 mL). The organic layers were combined, dried ($Na_2SO_4$) and the solvent removed in vacuo. The residue was purified by gradient flash column chromatography eluting with 3-6% MeOH in DCM to afford 1-(4-(3-fluoro-5-(trifluoromethyl)benzyl)pyridin-2-yl)-4,5,6,7-tetrahydro-1H-benzo[d][1,2,3]triazol-4-amine (200 mg, 47%) as a brown semi-solid. A small portion (30 mg) was further purified by prep HPLC (Method 2-40-70% gradient) to give the title compound (11 mg). Data in table 3.

Procedure 2

Example 2, N-(1-(4-(3-fluoro-5-(trifluoromethyl)benzyl)pyridin-2-yl)-4,5,6,7-tetrahydro-1H-benzo[d][1,2,3]triazol-4-yl)acetamide

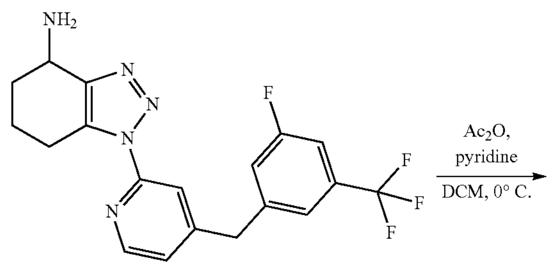

-continued

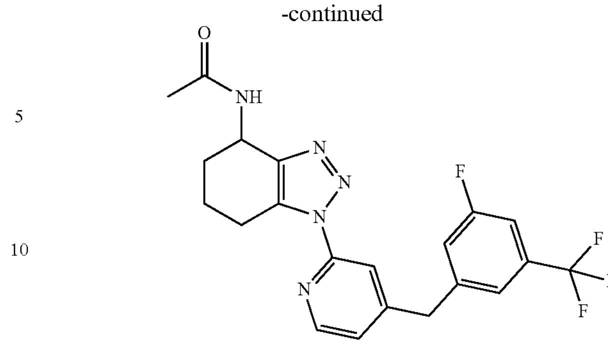

Pyridine (0.15 mL, 1.9 mmol) and $Ac_2O$ (0.1 mL) were added to a stirred solution of 1-(4-(3-fluoro-5-(trifluoromethyl)benzyl)pyridin-2-yl)-4,5,6,7-tetrahydro-1H-benzo[d][1,2,3]triazol-4-amine (Example 1, 75 mg, 0.19 mmol) in DCM (3 mL) and the reaction mixture was stirred at 0° C. for 3 h. The solvent was removed in vacuo and the residue was purified by trituration with $Et_2O$ and hexane to afford N-(1-(4-(3-fluoro-5-(trifluoromethyl)benzyl)pyridin-2-yl)-4,5,6,7-tetrahydro-1H-benzo[d][1,2,3]triazol-4-yl)acetamide (21 mg, 25%) as a white solid. Data in table 3.

Procedure 3

Example 3, N-(1-(4-(3-fluoro-5-(trifluoromethyl)benzyl)pyridin-2-yl)-4,5,6,7-tetrahydro-1H-benzo[d][1,2,3]triazol-4-yl)propionamide

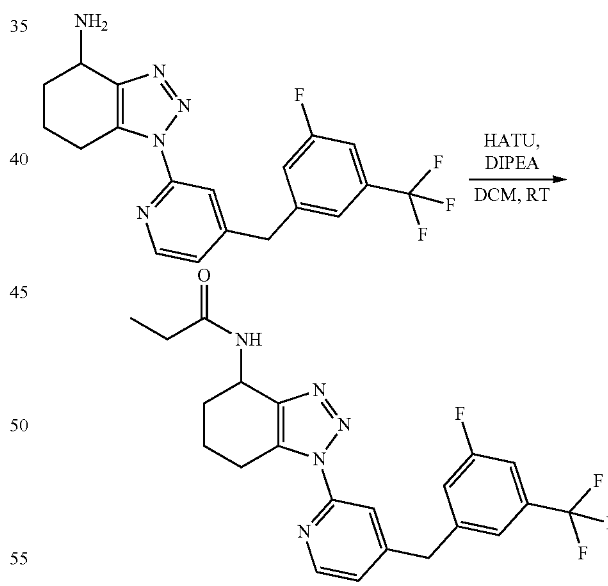

1-(4-(3-fluoro-5-(trifluoromethyl)benzyl)pyridin-2-yl)-4,5,6,7-tetrahydro-1H-benzo[d][1,2,3]triazol-4-amine (Example 1, 50 mg, 0.13 mmol), HATU (58 mg, 0.15 mmol), propionic acid (0.01 mL, 0.14 mmol) and DIPEA (0.03 mL, 0.15 mmol) were added to DCM (5 mL) and the reaction mixture was stirred at RT for 3 h. The reaction mixture was partitioned between EtOAc (30 mL) and saturated aq $NaHCO_3$ solution (30 mL). The organic layer was separated, dried ($MgSO_4$) and solvent removed in vacuo. The residue was triturated with $Et_2O$ to afford N-(1-(4-(3-fluoro-5-(trifluoromethyl)benzyl)pyridin-2-yl)-4,5,6,7-tetrahydro-1H-benzo[d][1,2,3]triazol-4-yl)propionamide (32 mg, 56%). Data in table 3.

Procedure 4

Example 6, N-(1-(4-(3-fluoro-5-(trifluoromethyl)phenoxy)pyridin-2-yl)-4,5,6,7-tetrahydro-1H-benzo[d][1,2,3]triazol-4-yl)acetamide

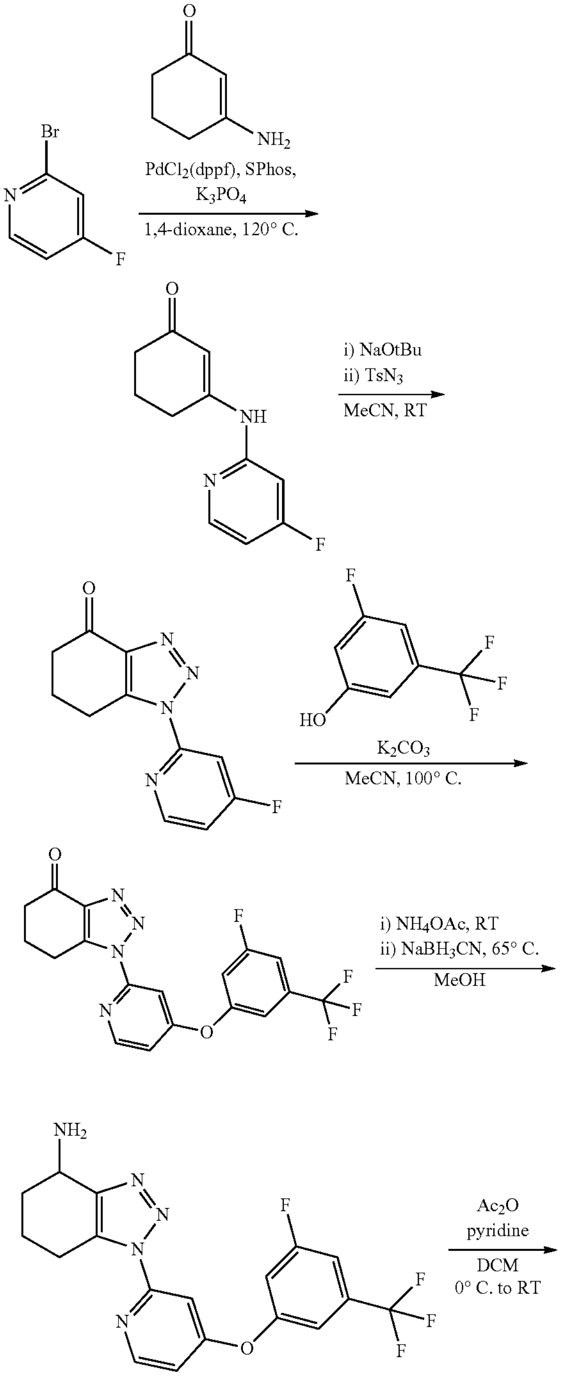

-continued

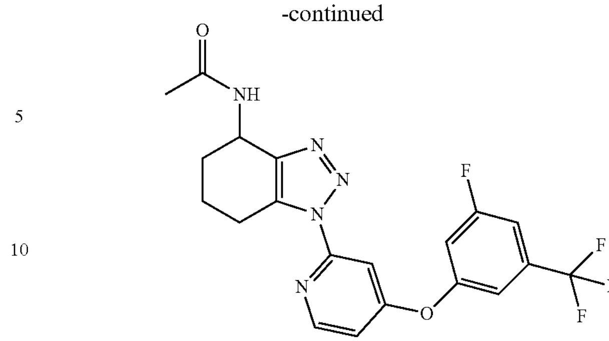

Step 1. 3-Aminocyclohex-2-en-1-one (632 mg, 5.68 mmol) was added to a stirred solution of 2-bromo-4-fluoropyridine (1.00 g, 5.68 mmol) in 1,4-dioxane (3.00 mL). The reaction mixture was degassed with argon for 10 min and $PdCl_2$(dppf) (371 mg, 0.455 mmol), $K_3PO_4$ (3.62 g, 17 mmol) and SPhos (117 mg, 0.284 mmol) were added to the reaction mixture. The reaction mixture was heated at 120° C. for 16 h and then quenched with water (20 mL) and aqueous layer was extracted with EtOAc (2×30 mL). The combined organic layers were dried ($Na_2SO_4$) and the solvent removed in vacuo. The residue was purified by gradient flash column chromatography eluting with 0-5% MeOH in DCM to afford 3-((4-fluoropyridin-2-yl)amino)cyclohex-2-en-1-one (400 mg, 32%) as a white solid.

LCMS (Method 9): m/z 207.1 (ES+), at 1.18 min.

Step 2. A solution of 3-((4-fluoropyridin-2-yl)amino)cyclohex-2-en-1-one (300 mg, 1.45 mmol) in MeCN (8 mL) was added dropwise to a suspension of sodium tert-butoxide (212 mg, 2.18 mmol) in MeCN (9 mL). After 30 min stirring at RT, a solution of tosyl azide (373 mg, 1.89 mmol) in MeCN (3 mL) was added dropwise. The reaction mixture was stirred for 1 h at RT and water (20 mL) was added. The aqueous layer was extracted with EtOAc (2×30 mL) and the combined organic layers were dried ($Na_2SO_4$) and the solvent removed in vacuo. The residue was purified by gradient flash column chromatography eluting with 30-40% EtOAc in hexane to afford 1-(4-fluoropyridin-2-yl)-1,5,6,7-tetrahydro-4H-benzo[d][1,2,3]triazol-4-one (200 mg, 57%) as a brown solid.

LCMS (Method 9): m/z 233.2 (ES+), at 1.38 min.

Step 3. $K_2CO_3$ (143 mg, 1.03 mmol) was added to a stirred solution of 3-fluoro-5-(trifluoromethyl)phenol (155 mg, 0.86 mmol) in MeCN (4 mL) and the reaction mixture stirred at RT for 10 min. 1-(4-fluoropyridin-2-yl)-1,5,6,7-tetrahydro-4H-benzo[d][1,2,3]triazol-4-one (200 mg, 0.86 mmol) then was added and the reaction mixture heated at 100° C. for 24 h. The reaction mixture was poured into water (20 mL) and the aqueous layer was extracted with EtOAc (2×30 mL). The combined organic layers were dried ($Na_2SO_4$) and the solvent removed in vacuo to afford 1-(4-(3-fluoro-5-(trifluoromethyl)phenoxy)pyridin-2-yl)-1,5,6,7-tetrahydro-4H-benzo[d][1,2,3]triazol-4-one (230 mg, crude) as a yellow solid. The crude material was used in the next step without further purification.

LCMS (Method 9): m/z 393.0 (ES+), at 2.36 min.

Step 4. Ammonium acetate (147 mg, 1.9 mmol) was added to a stirred solution of 1-(4-(3-fluoro-5-(trifluoromethyl)phenoxy)pyridin-2-yl)-1,5,6,7-tetrahydro-4H-benzo[d][1,2,3]triazol-4-one (75 mg, 0.19 mmol) in MeOH (3 mL) and the reaction mixture was stirred at RT for 16 h. $NaBH_3CN$ (36 mg, 0.57 mmol) was then added at 0° C. and the reaction mixture was heated at 65° C. for 16 h. The solvent was removed in vacuo and the residue was quenched with aq $NaHCO_3$ solution (20 mL). The aqueous layer was extracted with 10% MeOH in DCM (2×30 mL). The organic layers were combined, dried ($Na_2SO_4$) and the solvent removed in vacuo to afford 1-(4-(3-fluoro-5-(trifluoromethyl)phenoxy)pyridin-2-yl)-4,5,6,7-tetrahydro-1H-benzo[d][1,2,3]triazol-4-amine (Example 22) (73 mg, crude) as a brown gum. The crude material was used in the next step without further purification.

LCMS: Not recorded.

Step 5. Pyridine (0.07 mL, 0.91 mmol) and $Ac_2O$ (0.05 mL, 0.54 mmol) were added to a stirred solution of 1-(4-(3-fluoro-5-(trifluoromethyl)phenoxy)pyridin-2-yl)-4,5,6,7-tetrahydro-1H-benzo[d][1,2,3]triazol-4-amine (72 mg, 0.18 mmol) in DCM (4 mL) at 0° C. The reaction mixture was stirred at RT for 16 h. The solvent was removed in vacuo and the residue was purified by gradient flash column chromatography eluting with 70-80% EtOAc in hexane to afford N-(1-(4-(3-fluoro-5-(trifluoromethyl)phenoxy)pyridin-2-yl)-4,5,6,7-tetrahydro-1H-benzo[d][1,2,3]triazol-4-yl)acetamide (15 mg, 19%) as a white solid. Data in table 3.

Procedure 5

Example 7, 1-(4-(3-fluoro-5-(trifluoromethyl)benzyl)pyridin-2-yl)-N-methyl-4,5,6,7-tetrahydro-1H-benzo[d][1,2,3]triazol-4-amine

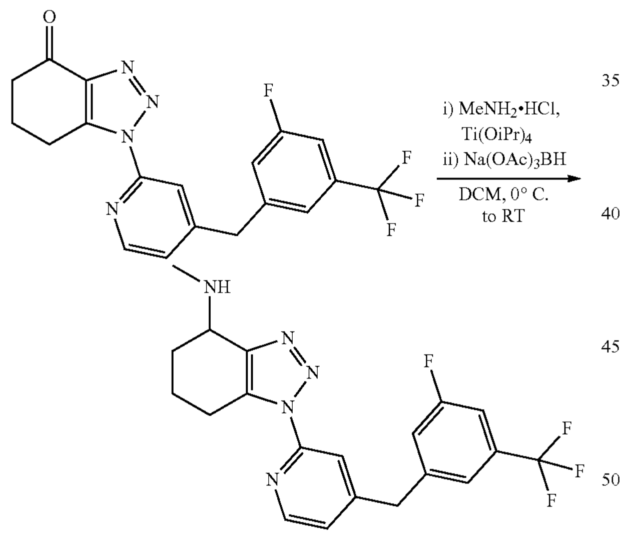

$Ti(OiPr)_4$ (155 mg, 0.53 mmol) was added to a stirred solution of 1-(4-(3-fluoro-5-(trifluoromethyl)benzyl)pyridin-2-yl)-1,5,6,7-tetrahydro-4H-benzo[d][1,2,3]triazol-4-one (Intermediate 1, 70 mg, 0.18 mmol) and methylamine hydrochloride (33 mg, 1.08 mmol) in DCM (2.9 mL) and the reaction mixture stirred at 0° C. for 4 h. $Na(OAc)_3BH$ (113 mg, 0.53 mmol) was added at 0° C. and the reaction mixture stirred at RT for 16 h. The reaction mixture was quenched with saturated aq $NaHCO_3$ solution (7.2 mL). The aqueous layer was extracted with DCM (2×10 mL). The organic layers were combined, dried ($Na_2SO_4$) and the solvent removed in vacuo. The residue was purified by prep HPLC (Method 1-10-75% gradient) to afford 1-(4-(3-fluoro-5-(trifluoromethyl)benzyl)pyridin-2-yl)-N-methyl-4,5,6,7-tetrahydro-1H-benzo[d][1,2,3]triazol-4-amine (47 mg, 65%) as a white semi-solid. Data in table 3.

Procedure 6

Example 9, 1-(4-(3-fluoro-5-(trifluoromethyl)benzyl)pyridin-2-yl)-N-(oxetan-3-yl)-4,5,6,7-tetrahydro-1H-benzo[d][1,2,3]triazol-4-amine

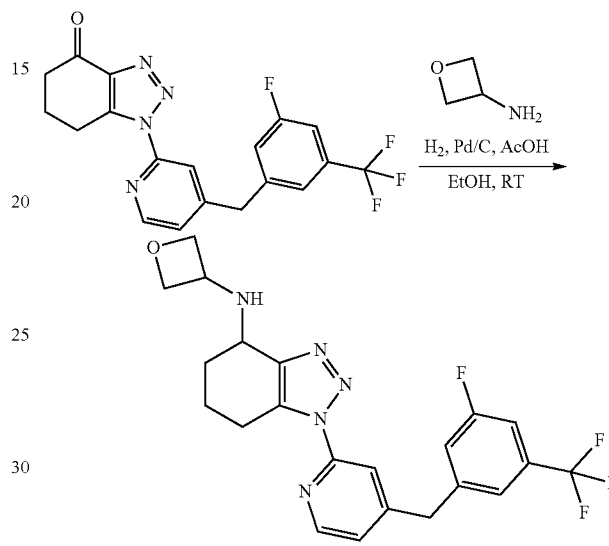

10% Palladium on carbon (13 mg) and acetic acid (0.02 mL) were added to a stirred solution of 1-(4-(3-fluoro-5-(trifluoromethyl)benzyl)pyridin-2-yl)-1,5,6,7-tetrahydro-4H-benzo[d][1,2,3]triazol-4-one (Intermediate 1, 100 mg, 0.26 mmol) and 3-oxetanamine (112 mg, 1.54 mmol) in EtOH (0.78 mL). The reaction mixture was stirred under $H_2$ at RT for 16 h. The reaction mixture was filtered through a pad of Celite which was washed twice with EtOH. The solvent was removed in vacuo. The residue was purified by prep HPLC (Method 1-10-85% gradient) to afford 1-(4-(3-fluoro-5-(trifluoromethyl)benzyl)pyridin-2-yl)-N-(oxetan-3-yl)-4,5,6,7-tetrahydro-1H-benzo[d][1,2,3]triazol-4-amine (19 mg, 17%) as a colourless semi-solid. Data in table 3.

Procedure 7

Example 11, N-(1-(4-(3-(trifluoromethyl)benzyl)pyridin-2-yl)-4,5,6,7-tetrahydro-1H-benzo[d][1,2,3]triazol-4-yl)acetamide

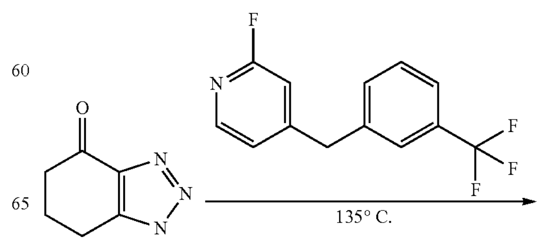

-continued

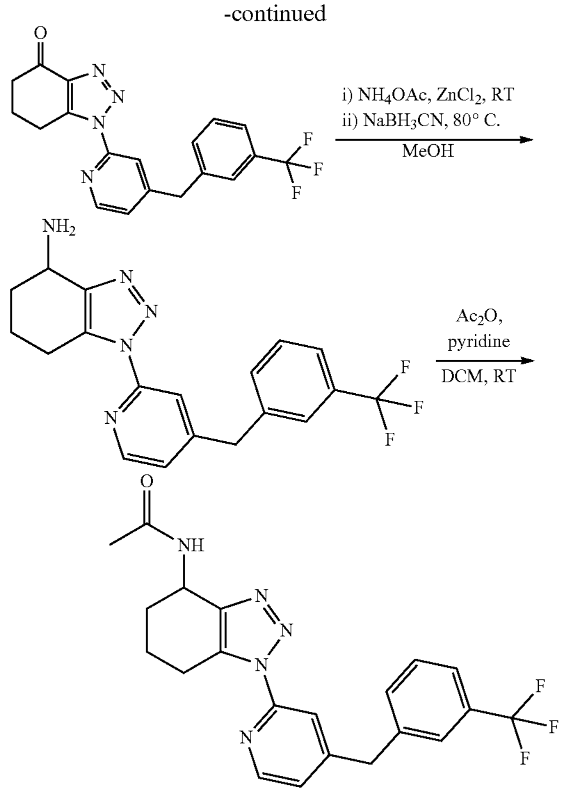

Step 1. 2-Fluoro-4-(3-(trifluoromethyl)benzyl)pyridine (Intermediate 2, 465 mg, 1.82 mmol) was added to 1,5,6,7-tetrahydro-4H-benzo[d][1,2,3]triazol-4-one (Intermediate 3, 250 mg, 1.82 mmol) and the reaction mixture heated at 135° C. for 16 h. The reaction mixture was dissolved in 5% MeOH/DCM (10 mL) and the solvent removed in vacuo to afford 1-(4-(3-(trifluoromethyl)benzyl)pyridin-2-yl)-1,5,6,7-tetrahydro-4H-benzo[d][1,2,3]triazol-4-one (100 mg, crude). The crude material was used in the next step without further purification.

MS (Method 1): m/z 373 (ES+).

Step 2. $ZnCl_2$ (493 mg, 3.62 mmol) was added to a stirred solution of 1-(4-(3-(trifluoromethyl)benzyl)pyridin-2-yl)-1,5,6,7-tetrahydro-4H-benzo[d][1,2,3]triazol-4-one (450 mg, 1.20 mmol) and ammonium acetate (924 mg, 12 mmol) in MeOH (12 mL) and the reaction mixture was stirred at RT for 7 h. $NaBH_3CN$ (224 mg, 3.62 mmol) was the added and the reaction mixture heated at 80° C. for 16 h. The reaction mixture was quenched with aq $NaHCO_3$ solution (30 mL) and the aqueous layer extracted with EtOAc (3×50 mL). The organic layers were combined, dried ($Na_2SO_4$) and the solvent removed in vacuo to afford 1-(4-(3-(trifluoromethyl)benzyl)pyridin-2-yl)-4,5,6,7-tetrahydro-1H-benzo[d][1,2,3]triazol-4-amine (Example 23) (400 mg, crude) as brown gel. The crude material was used in the next step without further purification.

MS (Method 1): m/z 374 (ES+).

Step 3. Pyridine (0.8 mL, 10.7 mmol) and $Ac_20$ (1.01 mL, 10.7 mmol) were added to a stirred solution of 1-(4-(3-(trifluoromethyl)benzyl)pyridin-2-yl)-4,5,6,7-tetrahydro-1H-benzo[d][1,2,3]triazol-4-amine (400 mg, 1.07 mmol) in DCM (6 mL) and the reaction mixture stirred at RT for 1 h. The solvent was removed in vacuo and the residue was purified by prep HPLC (Method 3-40-50% gradient) to afford N-(1-(4-(3-(trifluoromethyl)benzyl)pyridin-2-yl)-4,5,6,7-tetrahydro-1H-benzo[d][1,2,3]triazol-4-yl)acetamide (30 mg, 6%) as a white solid. Data in table 3.

Procedure 8

Example 12, N-(1-(4-(3-(difluoromethoxy)-5-fluorobenzyl)pyridin-2-yl)-4,5,6,7-tetrahydro-1H-benzo[d][1,2,3]triazol-4-yl)acetamide

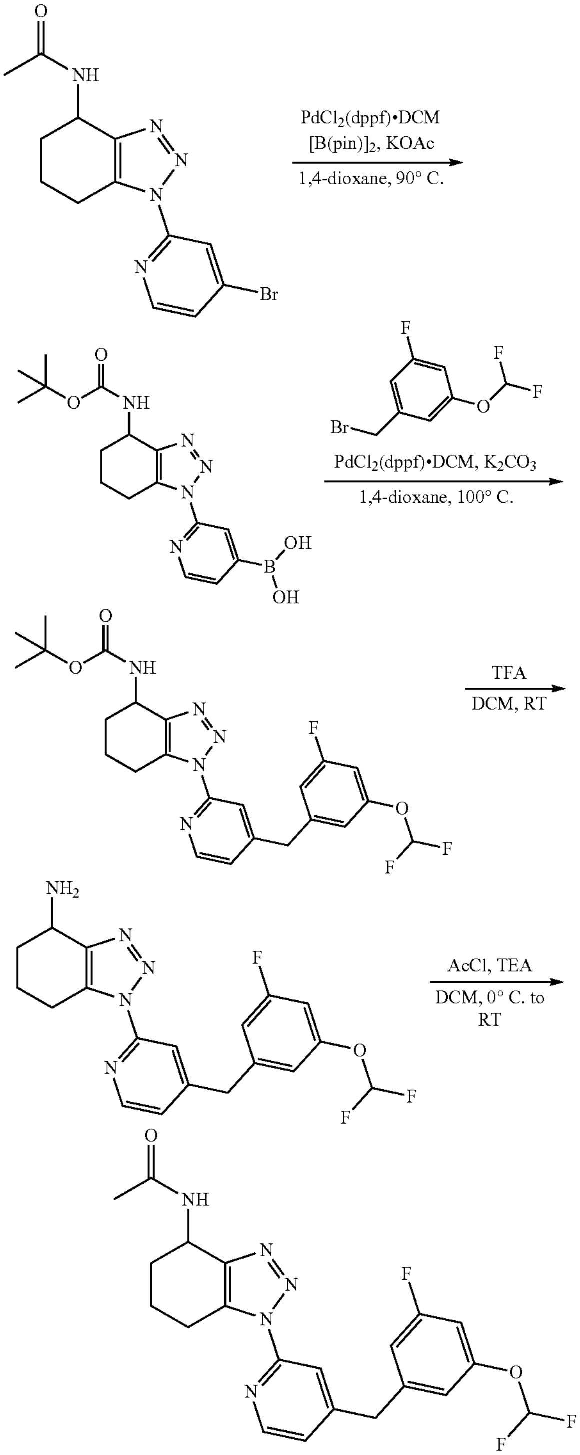

Step 1. KOAc (264 mg, 2.69 mmol) and $[B(pin)]_2$ (354 mg, 1.4 mmol) were added to a stirred solution of tert-butyl (1-(4-bromopyridin-2-yl)-4,5,6,7-tetrahydro-1H-benzo[d][1,2,3]triazol-4-yl)carbamate (425 mg, 1.07 mmol) in 1,4-dioxane (20 mL) at RT followed by the addition of $PdCl_2$(dppf).DCM (44 mg, 0.053 mmol). The resultant reaction mixture was heated at 90° C. for 12 h. The reaction mixture was filtered through Celite which was washed with 1,4-dioxane (40 mL). The filtrate was concentrated in vacuo to afford (2-(4-((tert-butoxycarbonyl)amino)-4,5,6,7-tetrahydro-1H-benzo[d][1,2,3]triazol-1-yl)pyridin-4-yl)boronic acid (900 mg, crude) as a brown gum. The crude material was used in the next step without further purification.

LCMS (Method 6): m/z 360.1 (ES+), at 1.70 min.

Step 2. $K_2CO_3$ (161 mg, 1.167 mmol) was added to a degassed solution of (2-(4-((tert-butoxycarbonyl)amino)-4,5,6,7-tetrahydro-1H-benzo[d][1,2,3]triazol-1-yl)pyridin-4-yl)boronic acid (140 mg, crude) and 1-(bromomethyl)-3-(difluoromethoxy)-5-fluorobenzene (99 mg, 0.389 mmol) in 1,4-dioxane (5 mL) followed by the addition of Pd(dppf)$Cl_2$-DCM (31 mg, 0.0389 mmol) and the resultant reaction mixture was heated at 100° C. for 16 h. The reaction mixture was filtered through Celite which was washed with 1,4-dioxane (10 mL). The filtrate was concentrated in vacuo. The residue was purified by gradient flash column chromatography eluting with 0-40% EtOAc in pet-ether to afford tert-butyl (1-(4-(3-(difluoromethoxy)-5-fluorobenzyl)pyridin-2-yl)-4,5,6,7-tetrahydro-1H-benzo[d][1,2,3]triazol-4-yl)carbamate (80 mg, 42%) as a brown gum.

LCMS (Method 6): m/z 490.1 (ES+), at 2.69 min.

$^1$H NMR: (400 MHz, DMSO-$d_6$) δ: 8.49 (d, J=6.4 Hz, 1H), 7.97 (s, 1H), 7.48-7.45 (m, 1H), 7.29-7.00 (m, 5H), 4.82-4.76 (m, 1H), 4.02 (s, 2H), 3.06-2.90 (m, 2H), 1.99-1.75 (m, 4H), 1.43 (s, 9H).

Step 3. A suspension of tert-butyl (1-(4-(3-(difluoromethoxy)-5-fluorobenzyl)pyridin-2-yl)-4,5,6,7-tetrahydro-1H-benzo[d][1,2,3]triazol-4-yl)carbamate (80 mg, 0.163 mmol) in 20% TFA in DCM (10 mL) was stirred at RT for 2 h. The solvent was removed in vacuo and the residue was partitioned between EtOAc (10 mL) and 10% aq $NaHCO_3$ solution (10 mL). The organic layer was separated, dried ($Na_2SO_4$) and the solvent was removed in vacuo to afford 1-(4-(3-(difluoromethoxy)-5-fluorobenzyl)pyridin-2-yl)-4,5,6,7-tetrahydro-1H-benzo[d][1,2,3]triazol-4-amine (Example 24) (55 mg, 87%) as a colourless gum.

LCMS (Method 7): m/z 390.0 (ES+), at 2.23 min.

$^1$H NMR: (400 MHz, DMSO-$d_6$) δ: 8.49 (d, J=5.2 Hz, 1H), 7.98 (s, 1H), 7.48-7.44 (m, 1H), 7.29 (s, 1H), 7.21-7.00 (m, 3H), 4.16 (s, 2H), 4.15-4.11 (m, 1H), 3.05-2.97 (m, 2H), 1.99-1.91 (m, 2H), 1.74-1.58 (m, 2H). 2 exchangeable protons not observed.

Step 4. TEA (14 mg, 0.141 mmol) was added to a stirred solution of 1-(4-(3-(difluoromethoxy)-5-fluorobenzyl)pyridin-2-yl)-4,5,6,7-tetrahydro-1H-benzo[d][1,2,3]triazol-4-amine (55 mg, 0.141 mmol) in DCM (5 mL) at 0° C. followed by acetyl chloride (11 mg, 0.141 mmol). The resultant reaction mixture was stirred at RT for 30 min. The solvent was removed in vacuo and the residue was purified by prep HPLC (Method 4). The solvent was removed in vacuo and the residue partitioned between water (10 mL) and DCM (10 mL). The organic layer was separated, dried ($Na_2SO_4$) and the solvent removed in vacuo to afford N-(1-(4-(3-(difluoromethoxy)-5-fluorobenzyl)pyridin-2-yl)-4,5,6,7-tetrahydro-1H-benzo[d][1,2,3]triazol-4-yl)acetamide (14 mg, 23%) as an off-white solid. Data in table 3.

Procedure 9

Example 13, N-(1-(4-(3-(difluoromethyl)-5-fluorobenzyl)pyridin-2-yl)-4,5,6,7-tetrahydro-1H-benzo[d][1,2,3]triazol-4-yl)acetamide

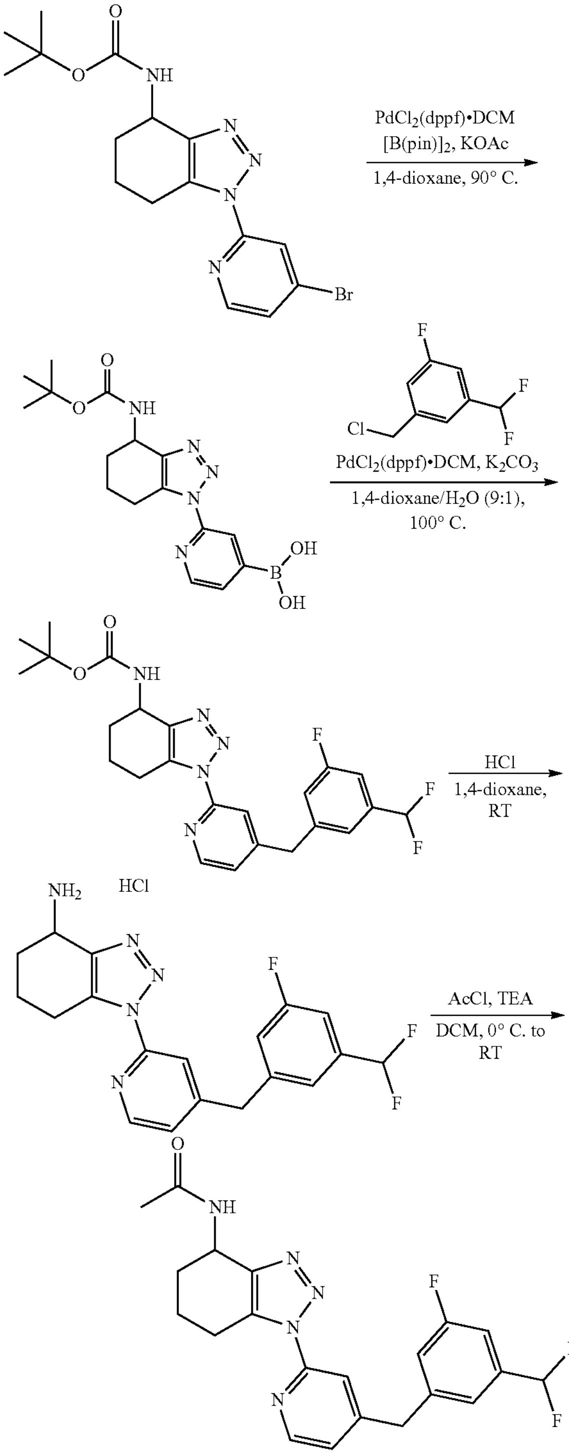

Steps 1 and 2. tert-Butyl (1-(4-(3-(difluoromethyl)-5-fluorobenzyl)pyridin-2-yl)-4,5,6,7-tetrahydro-1H-benzo[d][1,2,3]triazol-4-yl)carbamate (120 mg, 47%) was prepared from tert-butyl (1-(4-bromopyridin-2-yl)-4,5,6,7-tetrahydro-1H-benzo[d][1,2,3]triazol-4-yl)carbamate (Intermediate 4, 425 mg, 1.07 mmol) and 1-(chloromethyl)-3-(difluoromethyl)-5-fluorobenzene (Intermediate 5, 200 mg, 1.03 mmol) using the methods of Procedure 8, steps 1 and 2.

LCMS (Method 6): m/z 474.1 (ES+), at 2.60 min.

$^{1}$H NMR: (400 MHz, $CDCl_3$) δ: 8.43 (d, J=5.2 Hz, 1H), 7.99 (s, 1H), 7.17-7.13 (m, 3H), 7.06-7.02 (m, 1H), 6.63 (t, J=56.0 Hz, 1H), 5.03-4.93 (m, 1H), 4.13 (s, 2H), 2.00-1.85 (m, 2H), 1.65-1.40 (m, 4H), 1.13 (s, 9H). 1 exchangeable proton not observed.

Step 3. 4 N HCl in 1,4-dioxane (5 mL) was added to a suspension of tert-butyl (1-(4-(3-(difluoromethyl)-5-fluorobenzyl)pyridin-2-yl)-4,5,6,7-tetrahydro-1H-benzo[d][1,2,3]triazol-4-yl)carbamate (120 mg, 0.253 mmol) in 1,4-dioxane (5 mL) and the resultant reaction mixture was stirred at RT for 2 h. The reaction mixture was concentrated in vacuo to afford 1-(4-(3-(difluoromethyl)-5-fluorobenzyl)pyridin-2-yl)-4,5,6,7-tetrahydro-1H-benzo[d][1,2,3]triazol-4-amine hydrogen chloride (Example 15) (80 mg, 77%) as a colourless gum.

LCMS (Method 8): m/z 374.1 (ES+), at 1.35 min.

$^{1}$H NMR: (300 MHz, DMSO-$d_6$) δ: 8.55-8.45 (m, 3H), 8.03 (s, 1H), 7.51-7.45 (m, 4H), 7.34-7.31 (m, 1H), 7.03 (t, J=55.2 Hz, 1H), 4.65-4.55 (m, 1H), 4.25 (s, 2H), 3.70-3.50 (m, 2H), 2.20-2.00 (m, 4H).

Step 4. N-(1-(4-(3-(difluoromethyl)-5-fluorobenzyl)pyridin-2-yl)-4,5,6,7-tetrahydro-1H-benzo[d][1,2,3]triazol-4-yl)acetamide (16 mg, 20%) was prepared from 1-(4-(3-(difluoromethyl)-5-fluorobenzyl)pyridin-2-yl)-4,5,6,7-tetrahydro-1H-benzo[d][1,2,3]triazol-4-amine hydrogen chloride (80 mg, 0.20 mmol) using the methods of Procedure 8, step 4. Data in table 3.

Further examples prepared by the above procedures are detailed in Table 3.

TABLE 2

| Intermediates | | | |
|---|---|---|---|
| Intermediate | Name | Structure | Data |
| 1 | 1-(4-(3-fluoro-5-(trifluoromethyl)benzyl)pyridin-2-yl)-1,5,6,7-tetrahydro-4H-benzo[d][1,2,3]triazol-4-one | 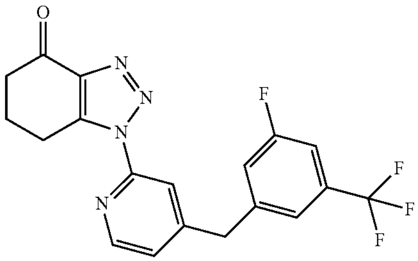 [SMILES: O=C1CCCc2c1nnn2-c1cc(Cc2cc(F)cc(C(F)(F)F)c2)ccn1] | LCMS (Method 10): m/z 391.3 (ES+), at 1.37 min. $^{1}$H NMR; (400 MHz, $CDCl_3$) δ: 8.49 (d, J = 5.1 Hz, 1H), 8.08 (s, 1H), 7.37-7.24 (m, 2H), 7.20 (dd, J = 5.1, 1.5 Hz, 1H), 7.13 (dt, J = 9.0, 1.9 Hz, 1H), 4.18 (s, 2H), 3.51 (t, J = 6.2 Hz, 2H), 2.70 (t, J = 7.3 Hz, 2H), 2.29 (p, J = 6.4 Hz, 2H). |
| 2 | 2-fluoro-4-(3-(trifluoromethyl)benzyl)pyridine | 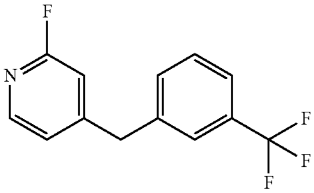 [SMILES: Fc1cc(Cc2cccc(C(F)(F)F)c2)ccn1] | LCMS (method 4): m/z 256.2 (ES+), at 1.52 min. $^{1}$H NMR: (400 MHz, Methanol-$d_4$) δ: 7.99 (dt, J = 5.2, 0.6 Hz, 1H), 7.52-7.35 (m, 4H), 7.06 (dddt, J = 5.2, 2.0, 1.3, 0.6 Hz, 1H), 6.83 (tq, J = 1.4, 0.7 Hz, 1H), 4.05 (s, 2H). |
| 3 | 1,5,6,7-tetrahydro-4H-benzo[d][1,2,3]triazol-4-one | 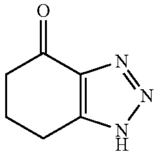 | MS (Method 1): m/z 138 (ES+). $^{1}$H NMR: (400 MHz, DMSO-$d_6$) δ: 2.91 (t, J = 6.0 Hz, 2H), 256-2.43 (m, 2H), 2.13-2.02 (m, 2H). 1 exchangeable proton not observed. |
| 4 | tert-butyl (1-(4-bromopyridin-2-yl)-4,5,6,7-tetrahydro-1H-benzo[d][1,2,3]triazol-4-yl)carbamate | 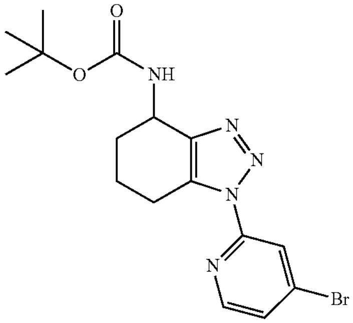 [SMILES: CC(C)(C)OC(=O)NC1CCCc2c1nnn2-c1cc(Br)ccn1] | LCMS (Method 6): m/z 394.0 (ES+), at 2.37 min. $^{1}$H NMR: (400 MHz, DMSO-$d_6$) δ: 8.50 (d, J = 5.2 Hz, 1H), 8.26 (s, 1H), 7.82 (dd, J = 1.6, 5.4 Hz, 1H), 7.26 (d, J = 8.4 Hz, 1H), 4.83-4.78 (m, 1H), 3.08-2.94 (m, 2H), 2.00-1.88 (m, 2H), 1.78-1.72 (m, 2H), 1.37 (s, 9H). |

TABLE 2-continued

| Intermediates | | | |
|---|---|---|---|
| Intermediate | Name | Structure | Data |
| 5 | 1-(chloromethyl)-3-(difluoromethyl)-5-fluorobenzene | 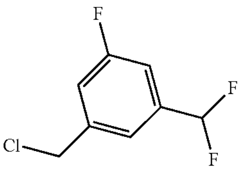 [SMILES: Fc1cc(CCl)cc(C(F)F)c1] | GCMS (Method 2): m/z 193.9 (ESI+), at 2.25 min. $^1$H NMR: Not recorded. |
| 6 | 1-(chloromethyl)-3-fluoro-5-(fluoromethyl)benzene | 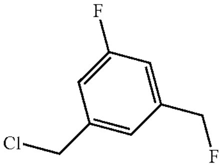 [SMILES: FCc1cc(F)cc(CCl)c1] | GCMS (Method 1): m/z 175.9 (ES+), at 6.25 min. $^1$H NMR: (400 MHz, DMSO-$d_6$) δ: 7.19 (s, 1H), 7.17-7.03 (m, 2H), 5.40 (d, J = 47.2 Hz, 2H), 4.59 (s, 2H). |

TABLE 3

| Examples | | | | |
|---|---|---|---|---|
| Ex. No. | Name | Intermediate/procedure | $^1$H NMR | LCMS |
| 1 | 1-(4-(3-fluoro-5-(trifluoromethyl)benzyl)pyridin-2-yl)-4,5,6,7-tetrahydro-1H-benzo[d][1,2,3]triazol-4-amine | Intermediate 1 Procedure 1 | (400 MHz, $CDCl_3$) δ: 8.42 (d, J = 5.1 Hz, 1H), 7.98 (d, J = 1.4 Hz, 1H), 7.36-7.18 (m, 2H), 7.16-7.02 (m, 2H), 4.21 (t, J = 6.1 Hz, 1H), 4.12 (s, 2H), 3.26-3.02 (m, 2H), 2.20-2.02 (m, 2H), 1.90-1.77 (m, 1H), 1.66 (m, 1H). 2 exchangeable protons not observed. | m/z 392.1 (M + H)+ (ES+), at 5.49 min, 97% (Method 5) |
| 1 - Isomer 1 | 1-(4-(3-fluoro-5-(trifluoromethyl)benzyl)pyridin-2-yl)-4,5,6,7-tetrahydro-1H-benzo[d][1,2,3]triazol-4-amine (Single enantiomer of unknown absolute stereochemistry) | Example 1 Chiral SFC method 1 (Isocratic run 15% co-solvent) Chiral SFC purity analysis: 1.81 min, 99% (Method 3 - 3-50% gradient) | (400 MHz, $CDCl_3$) δ: 8.42 (dd, J = 5.1, 0.7 Hz, 1H), 7.98 (dq, J = 1.4, 0.7 Hz, 1H), 7.34-7.17 (m, 2H), 7.17-7.04 (m, 2H), 4.21 (ddt, J = 7.4, 5.3, 1.2 Hz, 1H), 4.12 (d, J = 0.8 Hz, 2H), 3.20-3.08 (m, 2H), 2.21-1.97 (m, 2H), 1.91-1.75 (m, 1H), 1.67-1.59 (m, 1H). 2 exchangeable protons not observed. | Not recorded |
| 1 - Isomer 2 | 1-(4-(3-fluoro-5-(trifluoromethyl)benzyl)pyridin-2-yl)-4,5,6,7-tetrahydro-1H-benzo[d][1,2,3]triazol-4-amine (Single enantiomer of unknown absolute stereochemistry) | Example 1 Chiral SFC method 1 (Isocratic run 15% co-solvent) Chiral SFC purity analysis: 1.86 min, 94% (Method 3 - 3-50% gradient) | (400 MHz, $CDCl_3$) δ: 8.44 (dd, J = 5.1, 0.7 Hz, 1H), 8.00 (dq, J = 1.5, 0.7 Hz, 1H), 7.38-7.22 (m, 2H), 7.21-7.05 (m, 2H), 4.23 (t, J = 6.1 Hz, 1H), 4.15 (s, 2H), 3.20-3.10 (m, 2H), 2.23-2.02 (m, 2H), 1.94-1.80 (m, 1H), 1.69-1.62 (m, 1H). 2 exchangeable protons not observed. | Not recorded |
| 2 | N-(1-(4-(3-fluoro-5-(trifluoromethyl)benzyl)pyridin-2-yl)-4,5,6,7-tetrahydro-1H-benzo[d][1,2,3]triazol-4-yl)acetamide | Example 1 Procedure 2 | (400 MHz, DMSO-$d_6$) δ: 8.49 (d, J = 5.1 Hz, 1H), 8.26 (d, J = 8.0 Hz, 1H), 8.02 (s, 1H), 7.68 (s, 1H), 7.62 (d, J = 9.6 Hz, 1H), 7.56 (d, J = 8.6 Hz, 1H), 7.46 (d, J = 4.9 Hz, 1H), 5.06 (t, J = 3.7 Hz, 1H), 4.26 (s, 2H), 3.09-3.02 (m, 1H), 2.99-2.90 (m, 1H), 1.91-1.73 (m, 6H), 1.72-1.64 (m, 1H). | m/z 434.1 (M + H)+ (ES+), at 6.14 min, 100% (Method 3) |
| 2 - Isomer 1 | N-(1-(4-(3-fluoro-5-(trifluoromethyl)benzyl)pyridin-2-yl)-4,5,6,7-tetrahydro-1H-benzo[d][1,2,3]triazol-4-yl)acetamide (Single enantiomer of unknown absolute stereochemistry) | Example 2 Chiral SFC method 2 (Isocratic run 20% co-solvent) Chiral SFC purity analysis: 1.96 min, 98% (Method 4 - 3-50% gradient) | (400 MHz, DMSO-$d_6$) δ: 8.50 (dd, J = 5.1, 0.7 Hz, 1H), 8.26 (d, J = 8.1 Hz, 1H), 8.01 (dd, J = 1.5, 0.7 Hz, 1H), 7.68 (td, J = 1.6, 0.8 Hz, 1H), 7.62 (dt, J = 9.7, 2.0 Hz, 1H), 7.60-7.53 (m, 1H), 7.47 (dd, J = 5.1, 1.5 Hz, 1H), 5.07 (p, J = 4.4 Hz, 1H), 4.26 (s, 2H), 3.09 (dt, J = 17.5, 5.0 Hz, 1H), 2.93 (dt, J = 17.6, 6.4 Hz, 1H), 1.91-1.64 (m, 4H), 1.85 (s, 3H). | m/z 434.3 (M + H)+ (ES+), at 3.99 min, 100% (Method 2) |
| 2 - Isomer 2 | N-(1-(4-(3-fluoro-5-(trifluoromethyl)benzyl)pyridin-2-yl)-4,5,6,7-tetrahydro-1H-benzo[d][1,2,3]triazol-4-yl)acetamide (Single enantiomer of unknown absolute stereochemistry) | Example 2 Chiral SFC method 2 (Isocratic run 20% co-solvent) Chiral SFC purity analysis: 2.03 min, 99% (Method 4 - 3-50% gradient) | (400 MHz, DMSO-$d_6$) δ: 8.50 (dd, J = 5.1, 0.7 Hz, 1H), 8.26 (d, J = 8.1 Hz, 1H), 8.01 (dd, J = 1.5, 0.8 Hz, 1H), 7.68 (td, J = 1.5, 0.7 Hz, 1H), 7.62 (dt, J = 9.7, 1.8 Hz, 1H), 7.60-7.54 (m, 1H), 7.47 (dd, J = 5.1, 1.5 Hz, 1H), 5.12-5.03 (m, 1H), 4.26 (s, 2H), 3.09 (dt, J = 17.7, 5.0 Hz, 1H), 2.93 (dt, J = | m/z 434.3 (M + H)+ (ES+), at 3.99 min, 100% (Method 2) |

TABLE 3-continued

| Examples | | | | |
|---|---|---|---|---|
| Ex. No. | Name | Intermediate/procedure | $^1$H NMR | LCMS |
| | | | 17.6, 6.5 Hz, 1H), 1.91-1.60 (m, 4H), 1.85 (s, 3H). | |
| 3 | N-(1-(4-(3-fluoro-5-(trifluoromethyl)benzyl)pyridin-2-yl)-4,5,6,7-tetrahydro-1H-benzo[d][1,2,3]triazol-4-yl)propionamide | Example 1 and CAS: 79-09-4 Procedure 3 | (400 MHz, $CDCl_3$) δ: 8.43 (dd, J = 5.1, 0.7 Hz, 1H), 7.96 (dq, J = 1.5, 0.7 Hz, 1H), 7.31-7.21 (m, 2H), 7.15-7.04 (m, 2H), 5.90 (d, J = 6.7 Hz, 1H), 5.21 (q, J = 6.3 Hz, 1H), 4.13 (s, 2H), 3.22-3.08 (m, 2H), 2.36-2.16 (m, 3H), 2.02-1.83 (m, 2H), 1.77 (m, 1H), 1.19 (t, J = 7.6 Hz, 3H). | m/z 448.2 (M + H)+ (ES+), at 4.15 min, 100% (Method 2) |
| 4 | 2,2-difluoro-N-(1-(4-(3-fluoro-5-(trifluoromethyl)benzyl)pyridin-2-yl)-4,5,6,7-tetrahydro-1H-benzo[d][1,2,3]triazol-4-yl)acetamide | Example 1 and CAS: 381-73-7 Procedure 3 | (400 MHz, $CDCl_3$) δ: 8.43 (dd, J = 5.1, 0.7 Hz, 1H), 7.98 (dq, J = 1.4, 0.7 Hz, 1H), 7.34-7.19 (m, 2H), 7.18-7.05 (m, 2H), 6.68 (d, J = 7.0 Hz, 1H), 5.96 (t, J = 54.3 Hz, 1H), 5.28 (q, J = 3.8 Hz, 1H), 4.13 (s, 2H), 3.25-3.15 (m, 2H), 2.28 (dtd, J = 13.1, 5.2, 3.1 Hz, 1H), 2.03-1.82 (m, 3H). | m/z 470.2 (M + H)+ (ES+), at 4.89 min, 100% (Method 1) |
| 5 | 2-fluoro-NV-(1-(4-(3-fluoro-5-(trifluoromethyl)benzyl)pyridin-2-yl)-4,5,6,7-tetrahydro-1H-benzo[d][1,2,3]triazol-4-yl)acetamide | Example 1 and CAS: 144-49-0 Procedure 3 | (400 MHz, $CDCl_3$) δ: 8.36 (dd, J = 5.1, 0.7 Hz, 1H), 8.01-7.77 (m, 1H), 7.28-7.10 (m, 2H), 7.10-6.95 (m, 2H), 6.79-6.49 (m, 1H), 5.34-5.16 (m, 1H), 4.93-4.61 (m, 2H), 4.07 (s, 2H), 3.20-3.01 (m, 2H), 2.25-2.11 (m, 1H), 1.94-1.71 (m, 3H). | m/z 452.2 (M + H)+ (ES+), at 4.41 min, 100% (Method 1) |
| 6 | N-(1-(4-(3-fluoro-5-(trifluoromethyl)phenoxy)pyridin-2-yl)-4,5,6,7-tetrahydro-1H-benzo[d][1,2,3]triazol-4-yl)acetamide | CAS: 357927-50-5, 5220-49-5 and 172333-87-8 Procedure 4 | (400 MHz, DMSO-$d_6$) δ: 8.53 (d, J = 5.7 Hz, 1H), 8.26 (d, J = 8.0 Hz, 1H), 7.73-7.67 (m, 2H), 7.63 (s, 1H), 7.55 (d, J = 2.3 Hz, 1H), 7.20 (dd, J = 2.3 Hz, 5.7 Hz, 1H), 5.06 (t, J = 7.8 Hz, 1H), 3.13-3.08 (m, 1H), 2.96-2.92 (m, 1H), 1.90-1.78 (m, 6H), 1.73-1.65 (m, 1H). | m/z 436.1 (M + H)+ (ES+), at 6.20 min, 96% (Method 3) |
| 7 | 1-(4-(3-fluoro-5-(trifluoromethyl)benzyl)pyridin-2-yl)-N-methyl-4,5,6,7-tetrahydro-1H-benzo[d][1,2,3]triazol-4-amine | Intermediate 1 and CAS: 593-51-1 Procedure 5 | (400 MHz, DMSO-$d_6$) δ: 8.48 (d, J = 5.2 Hz, 1H), 7.99 (s, 1H), 7.67 (s, 1H), 7.62 (d, J = 9.6 Hz, 1H), 7.56 (d, J = 8.8 Hz, 1H), 7.45 (dd, J = 1.2 Hz, 5.2 Hz, 1H), 4.25 (s, 2H), 3.72 (bs, 1H), 3.08-3.00 (m, 1H), 2.96-2.88 (m, 1H), 2.44 (s, 3H), 1.96-1.89 (m, 2H), 1.75-1.68 (m, 3H). | m/z 406.2 (M + H)+ (ES+), at 5.48 min, 94% (Method 5) |
| 8 | 1-(4-(3-fluoro-5-(trifluoromethyl)benzyl)pyridin-2-yl)-N-(2-methoxyethyl)-4,5,6,7-tetrahydro-1H-benzo[d][1,2,3]triazol-4-amine | Intermediate 1 and CAS: 109-85-3 Procedure 5 | (400 MHz, DMSO-$d_6$) δ: 8.48 (d, J = 4.8 Hz, 1H), 7.99 (s, 1H), 7.67 (s, 1H), 7.62 (d, J = 9.2 Hz, 1H), 7.56 (d, J = 8.8 Hz, 1H), 7.45 (d, J = 4.8 Hz, 1H), 4.28 (s, 2H), 3.86 (s, 1H), 3.43 (t, J = 5.2 Hz, 2H), 3.25 (s, 3H), 3.05-2.99 (m, 1H), 2.97-2.91 (m, 2H), 2.88-2.81 (m, 1H), 2.03-1.78 (m, 3H), 1.74-1.67 (m, 2H). | m/z 450.27 (M + H)+ (ES+), at 6.11 min, 90% (Method 5) |
| 9 | 1-(4-(3-fluoro-5-(trifluoromethyl)benzyl)pyridin-2-yl)-N-(oxetan-3-yl)-4,5,6,7-tetrahydro-1H-benzo[d][1,2,3]triazol-4-amine | Intermediate 1 and CAS: 21635-88-1 Procedure 6 | (400 MHz, DMSO-$d_6$) δ: 8.49 (d, J = 5.1 Hz, 1H), 8.00 (s, 1H), 7.68 (s, 1H), 7.62 (d, J = 9.7 Hz, 1H), 7.56 (d, J = 8.9 Hz, 1H), 7.48-7.41 (m, 1H), 4.66 (dt, J = 10.9, 6.4 Hz, 2H), 4.39 (t, J = 6.1 Hz, 1H), 4.31-4.14 (m, 4H), 3.83 (t, J = 4.8 Hz, 1H), 3.29 (s, 2H), 3.04 (dt, J = 17.5, 5.4 Hz, 1H), 2.92 (dt, J = 17.5, 6.5 Hz, 1H), 1.94 (td, J = 12.5, 11.6, 6.7 Hz, 1H), 1.86-1.57 (m, 2H). | m/z 448.2 (M + H)+ (ES+), at 5.46 min, 100% (Method 3) |
| 10 | 1-(4-(3-fluoro-5-(trifluoromethyl)benzyl)pyridin-2-yl)-N-(tetrahydrofuran-3-yl)-4,5,6,7-tetrahydro-1H-benzo[d][1,2,3]triazol-4-amine | Intermediate 1 and CAS: 88675-24-5 Procedure 6 | (400 MHz, DMSO-$d_6$) δ: 8.49 (d, J = 5.1 Hz, 1H), 7.98 (s, 1H), 7.68 (s, 1H), 7.62 (d, J = 9.8 Hz, 1H), 7.57 (d, J = 8.9 Hz, 1H), 7.45 (d, J = 5.1 Hz, 1H), 4.26 (s, 2H), 4.00-3.58 (m, 5H), 3.55-3.35 (m, 1H), 3.30 (s, 2H), 3.04 (dt, J = 18.2, 5.5 Hz, 1H), 2.91 (ddd, J = 17.3, 8.0, 5.2 Hz, 1H), 2.16-1.88 (m, 2H), 1.88-1.57 (m, 3H). | m/z 462.2 (M + H)+ (ES+), at 5.54 min, 99% (Method 3) |
| 11 | N-(1-(4-(3-(trifluoromethyl)benzyl)pyridin-2-yl)-4,5,6,7-tetrahydro-1H-benzo[d][1,2,3]triazol-4-yl)acetamide | Intermediates 2 and 3 Procedure 7 | (400 MHz, DMSO-$d_6$) δ: 8.49 (d, J = 5.1 Hz, 1H), 8.25 (d, J = 8.0 Hz, 1H), 7.96 (s, 1H), 7.77 (s, 1H), 7.72-7.52 (m, 3H), 7.44 (dd, J = 5.1, 1.5 Hz, 1H), 5.06 (dt, J = 8.2, 4.4 Hz, 1H), 4.25 (s, 2H), 3.08 (dt, J = 17.7, 5.0 Hz, 1H), | m/z 416.3 (M + H)+ (ES+), at 5.86 min, 98% (Method 5) |

TABLE 3-continued

| Examples | | | | |
|---|---|---|---|---|
| Ex. No. | Name | Intermediate/procedure | $^1$H NMR | LCMS |
| | | | 2.93 (dt, J = 17.8, 6.5 Hz, 1H), 1.97-1.59 (m, 4H), 1.84 (s, 3H). | |
| 12 | N-(1-(4-(3-(difluoromethoxy)-5-fluorobenzyl)pyridin-2-yl)-4,5,6,7-tetrahydro-1H-benzo[d][1,2,3]triazol-4-yl)acetamide | Intermediate 4 and CAS: 1017779-39-3 Procedure 8 | (400 MHz, DMSO-$d_6$) δ: 8.50 (d, J = 5.2 Hz, 1H), 8.29-8.27 (m, 1H), 7.97 (s, 1H), 7.46-7.45 (m, 1H), 7.29 (t, J = 73.6 Hz, 1H), 7.17-7.15 (m, 1H), 7.11-7.09 (m, 1H), 7.04-7.01 (m, 1H), 5.09-5.07 (m, 1H), 4.17 (s, 2H), 3.12-2.96 (m, 2H), 1.87-1.87 (m, 4H), 1.80 (s, 3H). | m/z 432.2 (M + H)+ (ES+), at 2.24 min, 100% (Method 7) |
| 13 | N-(1-(4-(3-(difluoromethyl)-5-fluorobenzyl)pyridin-2-yl)-4,5,6,7-tetrahydro-1H-benzo[d][1,2,3]triazol-4-yl)acetamide | Intermediates 4 and 5 Procedure 9 | (400 MHz, DMSO-$d_6$) δ: 8.51 (d, J = 5.6 Hz, 1H), 8.28 (d, J = 8.0 Hz, 1H), 7.98 (s, 1H), 7.50-7.45 (m, 3H), 7.34-7.32 (m, 1H), 7.03 (t, J = 55.2 Hz, 1H), 5.08-5.07 (m, 1H), 4.24 (s, 2H), 3.13-3.07 (m, 1H), 2.98-2.92 (m, 1H), 1.85 (s, 3H), 1.80-1.69 (m, 4H). | m/z 416.1 (M + H)+ (ES+), at 1.87 min, 100% (Method 6) |
| 13 - Isomer 1 | N-(1-(4-(3-(difluoromethyl)-5-fluorobenzyl)pyridin-2-yl)-4,5,6,7-tetrahydro-1H-benzo[d][1,2,3]triazol-4-yl)acetamide (Single enantiomer of unknown absolute stereochemistry) | Example 13 Chiral SFC method 5 (Isocratic run 15% co-solvent) Chiral SFC purity analysis: 1.64 min, 99% (Method 6 - 3-50% gradient) | (400 MHz, $CD_3OD$) δ: 8.46 (dd, J = 5.1, 0.7 Hz, 1H), 7.93 (dt, J = 1.6, 0.7 Hz, 1H), 7.41-7.28 (m, 2H), 7.28-7.12 (m, 2H), 7.01-6.38 (m, 1H), 5.24-5.12 (m, 1H), 4.21 (s, 2H), 3.25-2.98 (m, 2H), 2.07-1.70 (m, 4H), 1.99 (s, 3H). 1 exchangeable proton not observed. | m/z 416.2 (M + H)+ (ES+), at 3.58 min, 100% (Method 2) |
| 13 - Isomer 2 | N-(1-(4-(3-(difluoromethyl)-5-fluorobenzyl)pyridin-2-yl)-4,5,6,7-tetrahydro-1H-benzo[d][1,2,3]triazol-4-yl)acetamide (Single enantiomer of unknown absolute stereochemistry) | Example 13 Chiral SFC method 5 (Isocratic run 15% co-solvent) Chiral SFC purity analysis: 1.89 min, 94% (Method 6 - 3-50% gradient) | (400 MHz, $CD_3OD$) δ: 8.46 (dd, J = 5.1, 0.7 Hz, 1H), 7.93 (dt, J = 1.6, 0.7 Hz, 1H), 7.41-7.28 (m, 2H), 7.28-7.12 (m, 2H), 7.01-6.38 (m, 1H), 5.24-5.12 (m, 1H), 4.21 (s, 2H), 3.25-2.98 (m, 2H), 2.07-1.70 (m, 4H), 1.99 (s, 3H). 1 exchangeable proton not observed. | m/z 416.2 (M + H)+ (ES+), at 3.58 min, 100% (Method 2) |
| 14 | N-(1-(4-(3-fluoro-5-(fluoromethyl)benzyl)pyridin-2-yl)-4,5,6,7-tetrahydro-1H-benzo[d][1,2,3]triazol-4-yl)acetamide | Intermediates 4 and 6 Procedure 9 | (400 MHz, DMSO-$d_6$) δ: 8.50 (d, J = 5.6 Hz, 1H), 8.28 (d, J = 8.0 Hz, 1H), 7.95 (s, 1H), 7.45 (dd, J = 1.2, 5.2 Hz, 1H), 7.29-7.26 (m, 2H), 7.16-7.14 (m, 1H), 5.42 (d, J = 47.2 Hz, 2H), 5.10-5.05 (m, 1H), 4.19 (s, 2H), 3.12-3.08 (m, 1H), 2.98-2.92 (m, 1H), 1.85 (s, 3H), 1.80-1.70 (m, 4H). | m/z 398.1 (M + H)+ (ES+), at 1.81 min, 100% (Method 6) |

Biological Activity

GPR52 Agonist Functional cAMP Assay

HEKf suspension cells were infected for 24 h with 0.1% v/v human GPR52 expressing BacMam virus, a modified baculovirus designed for mammalian gene expression. Following BacMam infection, cells were pelleted by centrifugation (335 g, 5 min), resuspended in cell freezing medium (Sigma) and frozen at −150° C. until required. On experiment day, 25 nL GPR52 compound dilutions, prepared in DMSO, were stamped onto proxiplates (PerkinElmer) by a LabCyte ECHO acoustic dispenser. Frozen cells were thawed and resuspended in assay stimulation buffer (Cisbio) containing 0.5 mM 3-iso-butyl-1-methylxanthine (IBMX, Sigma) to achieve a density of 2000 cells per well. 10 μl cells were added to assay plates using a Multidrop Combi Reagent Dispenser (ThermoFisher) before centrifugation (335 g, 1 min). Cells were incubated with compounds at 37° C. for 30 min prior to addition of cAMP detection reagents (HiRange cAMP kit, Cisbio) which were prepared according to the manufacturer's instructions. Plates were shaken for 1 h at room temperature before reading on a PHERAstar FS plate reader (BMG Labtech) using standard HTRF settings. HTRF ratios were obtained by dividing the acceptor emissions (665 nm) by the donor emissions (620 nm) and multiplying by 10,000. Data were normalised to DMSO (0%) and maximal 3-(2-(3-chloro-5-fluorobenzyl)benzo[b]thiophen-7-yl)-N-(2-methoxyethyl)benzamide (compound 7m in *J. Med. Chem.*, 2014, 57, 5226) responses (100%) and fit to a 4-parameter logistical fit to generate agonist $pEC_{50}$s and maximal responses which are presented in Table 4 below.

TABLE 4

| GPR52 $pEC_{50}$ data | | |
|---|---|---|
| Ex. No. | $PEC_{50}$ average | $E_{max}$ (%) |
| 1 | 7.6 | 100 |
| 1 Isomer 1 | 7.9 | 101 |
| 1 Isomer 2 | 7.2 | 97 |
| 2 | 7.3 | 86 |
| 2 Isomer 1 | 7.8 | 91 |
| 2 Isomer 2 | 5.6 | 78 |
| 3 | 7.6 | 96 |
| 4 | 7.6 | 87 |
| 5 | 7.4 | 94 |
| 6 | 6.9 | 89 |
| 7 | 7.5 | 98 |
| 8 | 7.3 | 94 |
| 9 | 7.0 | 93 |
| 10 | 7.5 | 94 |
| 11 | 6.7 | 91 |
| 12 | 7.5 | 87 |
| 13 | 7.9 | 93 |
| 13 Isomer 1 | 6.3 | 73 |
| 13 Isomer 2 | 8.3 | 93 |
| 14 | 7.3 | 90 |

Pharmacokinetic Profiling

The pharmacokinetic profiles of Example 2 were assessed in male Sprague-Dawley rats via intravenous (IV) and oral (per os, PO) routes of delivery. Pharmacokinetic data (mean values±standard deviation) for Example 2 of the invention are detailed in Table 5.

Methods: For pharmacokinetic analysis, groups of three male Sprague-Dawley rats, ranging in weight between 200 and 230 g, were administered a single dose of Example 2 via IV or PO route, using the doses, dose volumes and vehicles specified in Table 5. Following dosing, blood samples were taken at several time points (pre-dose, 2 min, 5 min, 15 min, 30 min, 1 h, 3 h, 6 h, 12 h and 24 h for IV administration and pre-dose, 5 min, 15 min, 30 min, 1 hr, 2 h, 4 h, 8 h, 12 h and 24 h for PO administration) via serial tail vein bleeds, and centrifuged to separate plasma for analysis by LC-MS/MS. WinNonlin v8.2 statistics software (Pharsight Corporation, California, USA) was used to generate pharmacokinetic parameters using non-compartmental analysis.

Brain Penetration

Plasma and brain exposure were evaluated to assess the brain penetration of Example 2, following IV administration. Unbound brain-to-plasma ratio ($K_{p,uu}$) was calculated, as detailed in Table 5, following experimental determination of binding in rat plasma and brain homogenate.

Methods: For brain penetration assessment, male Sprague-Dawley rats (n=3) were administered a single 1 mg/kg dose (formulated in 10% DMAC+10% Solutol HS15+80% saline) via the IV route. After 10 min post-dose, animals were sacrificed and brains extracted, homogenised with 2 volumes (w/v) of 50 mM sodium phosphate buffer (pH 7.4), and analysed by LC-MS/MS. Blood samples were removed at the same time point via tail vein bleed, centrifuged and the plasma analysed by LC-MS/MS.

To permit calculation of unbound brain-to-plasma ratio ($K_{p,uu}$), test compound binding in rat plasma and brain homogenate was performed, using Rapid Equilibrium Dialysis (RED). Test compound prepared in DMSO (1 μM final, 0.2% DMSO) was added to (i) undiluted male Sprague Dawley rat plasma and (ii) rat brain tissue homogenised with 2 volumes (w/v) of sodium phosphate buffer (pH 7.4), and dialysed against phosphate buffer for 5 h at 37° C. After incubation, the contents of each plasma/brain and buffer compartment were removed and mixed with equal volumes of control dialysed buffer or plasma/brain to maintain matrix similarity for analysis. Proteins were then precipitated by the addition of acetonitrile containing an analytical internal standard (allowing ratio of test compound versus internal standard to be derived), centrifuged and the supernatant removed for analysis by LC-MS/MS. Fraction unbound ($F_u$) in plasma and brain was calculated using the following formula, then used to correct total plasma and brain concentrations to derive the $K_{p,uu}$:

Fraction bound=(Total plasma or brain ratio)−(Total buffer ratio)/Total plasma or brain ratio Fraction unbound($F_u$,brain or plasma)=1−Fraction bound For correction of dilution in brain binding assay:

Undiluted $F_u$,brain=(1/dilution factor)/((1/$F_u$ diluted))−1)+(1/dilution factor)

Where dilution factor=4

TABLE 5

Example 2 pharmacokinetic data

| | Rat IV pharmacokinetics (n = 3) | | | |
|---|---|---|---|---|
| | Dose (mg/kg) | Dose volume (mL/kg) | Dosing vehicle | Clearance (mL/min/kg) |
| Example 2 | 1 | 5 | 10% DMAC + 10% Solutol HS15 + 80% saline | 5.5 ± 1.0 |
| | **Rat PO pharmacokinetics (n = 3)** | | | |
| | Dose (mg/kg) | Dose volume (mL/kg) | Dosing vehicle | Bioavailability (%) |
| Example 2 | 3 | 5 | 10% DMAC + 10% Solutol HS15 + 80% water | 88.2 ± 11.4 |
| | **Rat IV brain penetration, 10 min (n = 3)** | | | |
| | Dose (mg/kg) | Dose volume (mL/kg) | Dosing vehicle | $K_{p,uu}$ |
| Example 2 | 1 | 5 | 10% DMAC + 10% Solutol HS15 + saline | 0.35 ± 0.02 |

Attenuation of Caffeine-Induced Locomotor Activity in Rat

Caffeine, a non-selective adenosine receptor antagonist, is a psychostimulant which increases rodent locomotor activity principally via blockade of $A_2A$ receptors (*Br. J. Pharmacol.,* 2000, 129, 1465). These receptors are densely expressed on the terminals of GABAergic striatopallidal neurons in the indirect pathway of the basal ganglia, in which dopamine D2 receptors are co-expressed (*J. Comp. Neurol.,* 1998, 401, 163*; J. Comp. Neurol.,* 2001, 431, 331). Tonic activation of $A_2A$ receptors decreases the affinity of D2 receptors to dopamine and antagonism of $A_2A$ receptors facilitates dopaminergic signalling (*Curr. Pharm. Des.,* 2008, 14, 1468). A number of antipsychotic agents have been shown to block hyperlocomotion induced by caffeine (*Pharmacol. Biochem. Behav.,* 1994, 47, 89; Naunyn-Schmiedeberg's *Arch. Pharmacol.,* 2016, 389, 11).

Male Sprague-Dawley rats (200-250 g) were housed in groups with a 12 h light/dark cycle (lights on at 07.00), at an ambient temperature of 21±2° C. and with standard pelleted diet and water adlibitum. Testing was carried out in the light phase. On the day of the experiment, animals were habituated to the locomotor cages for a 60-minute period. Subsequently, they were dosed with vehicle or Example 2 Isomer 1 (0.1, 0.3, 1 and 3 mg/kg) by the oral route and returned to the appropriate locomotor cage. Example 2 Isomer 1 was formulated in a vehicle of 10% DMAC, 10% solutol (Kolliphor HS15) and 80% water (v/v/v). Sixty minutes later, animals were dosed with vehicle (saline) or caffeine (15 mg/kg) by the subcutaneous route. Locomotor activity was assessed for a 2 h period after caffeine treatment. Data are back-transformed means, adjusted for differences between treatment groups in activity during the 30 minutes prior to treatment with test compound or vehicle (n=10-12). Analysis was by general linear model with treatment, cohort and rack as factors. SEMs were calculated from the residuals of the statistical model. Example 2 Isomer 1 was compared to caffeine by Williams' test.

As shown in FIG. 1, treatment with Example 2 Isomer 1 caused a dose-dependent reduction of the caffeine-induced hyperlocomotor response, reaching statistical significance across all time points at 3 and 10 mg/kg.

BRIEF DESCRIPTION OF THE FIGURES

FIG. 1: The effect of acute treatment with Example 2 Isomer 1 (0.3, 1, 3 and 10 mg/kg, PO) on caffeine-induced hyperlocomotor activity. Significant differences vs caffeine are represented as † $p<0.05$, †† $p<0.01$, ††† $p<0.001$.

The invention claimed is:

1. A compound of Formula (1a):

(1a)

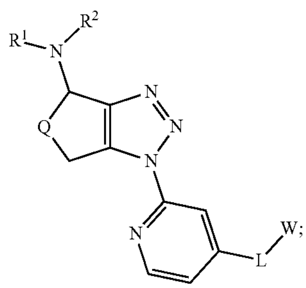

or a salt thereof, wherein;

$R^1$ is H, $C(O)C_{1-3}$ alkyl optionally substituted with 1 to 6 fluorine atoms, $C_{1-6}$ alkyl optionally substituted with 1 to 6 fluorine atoms or $C_{3-6}$ cycloalkyl optionally substituted with 1 to 6 fluorine atoms; wherein any one atom of the alkyl or cycloalkyl groups may be optionally replaced by O;

$R^2$ is H;

Q is selected from $—CR^3R^4—$, $—CR^3R^4CR^5R^6—$, $—CR^3R^4CR^5R^6CR^7R^8—$, $—CR^3R^4OCR^5R^6—$, $—CR^3R^4CR^5R^6O—$ and $—CR^3R^4O—$;

$R^3$, $R^4$, $R^5$, $R^6$, $R^7$ and $R^8$ are independently selected from H and $C_{1-3}$ alkyl;

L is selected from $CH_2$, CHOH and O;

and W is a moiety selected from:

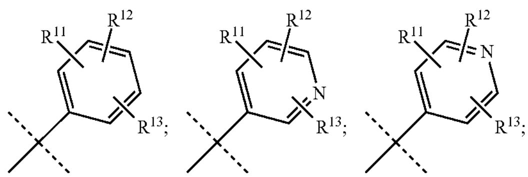

wherein $R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

2. The compound according to claim 1, which is a compound of Formula (2a):

(2a)

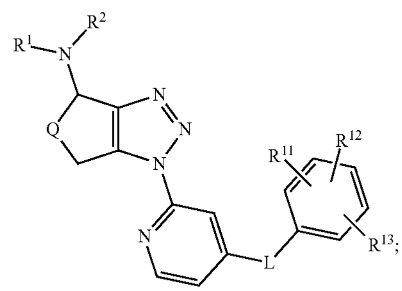

or a salt thereof, wherein;

$R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

3. The compound according to claim 1, wherein Q is selected from $—CH_2—$, $—CH_2CH_2—$, $—CH_2CH_2CH_2—$, $—CH_2CH_2O—$, $—CH_2OCH_2—$ and $—CH_2O—$.

4. The compound according to claim 1, wherein Q is $—CH_2CH_2—$.

5. The compound according to claim 1, which is a compound of Formula (3a):

(3a)

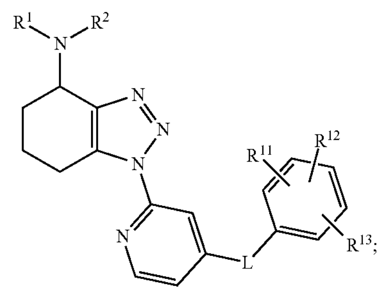

or a salt thereof, wherein;

$R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

6. The compound according to claim 1, wherein $R^1$ is selected from H, $CH_3$, $C(O)CH_3$, $C(O)CH_2CH_3$, $C(O)CF_2H$, $C(O)CF_3$, $C(O)CFH_2$, $CH_2CH_2OCH_3$, oxetane and oxolane.

7. The compound according to claim 6, wherein $R^1$ is $C(O)CH_3$.

8. The compound according to claim 1, which is a compound of Formula (4a):

(4a)

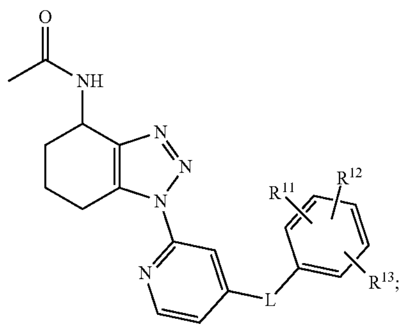

or a salt thereof, wherein;

$R^{11}$, $R^{12}$ and $R^{13}$ are independently selected from H, CN, halo, $C_{1-6}$ alkyl optionally substituted with 1 to 6 fluorine atoms and $C_{1-6}$ alkoxy optionally substituted with 1 to 6 fluorine atoms, wherein any one atom of the alkyl or alkoxy group may be optionally replaced by a heteroatom selected from O, N, S and oxidised forms thereof.

9. The compound according to claim 1, wherein L is $CH_2$.

10. The compound according to claim 1, wherein $R^{11}$, $R^{12}$ and $R^{13}$ are independently selected from H, F, $CF_3$, $CF_2H$, $CFH_2$ and $OCF_2H$.

11. The compound according to claim 1, wherein W is selected from the group consisting of:

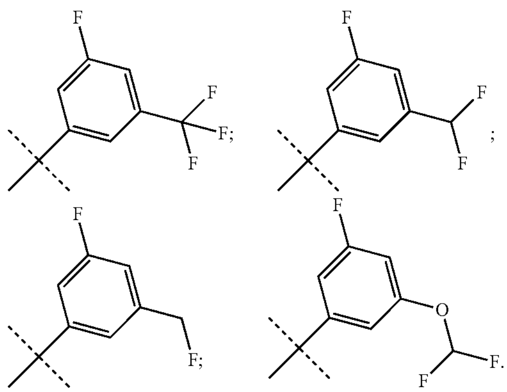

12. The compound according to claim 1, which is a compound of Formula (5):

(5)

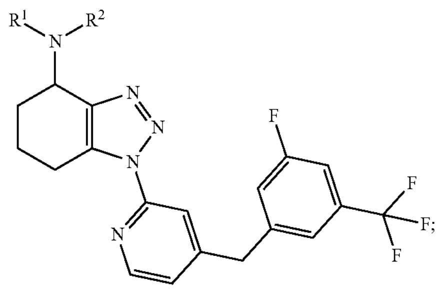

or a salt thereof.

13. The compound according to claim 1, which is selected from the group consisting of:

1-(4-{[3-fluoro-5-(trifluoromethyl)phenyl]methyl}pyridin-2-yl)-4,5,6,7-tetrahydro-1H-benzotriazol-4-amine;

N-[1-(4-{[3-fluoro-5-(trifluoromethyl)phenyl]methyl}pyridin-2-yl)-4,5,6,7-tetrahydro-1H-benzotriazol-4-yl]acetamide;

N-[1-(4-{[3-fluoro-5-(trifluoromethyl)phenyl]methyl}pyridin-2-yl)-4,5,6,7-tetrahydro-1H-benzotriazol-4-yl]propanamide;

2,2-difluoro-N-[1-(4-{[3-fluoro-5-(trifluoromethyl)phenyl]methyl}pyridin-2-yl)-4,5,6,7-tetrahydro-1H-benzotriazol-4-yl]acetamide;

2-fluoro-N-[1-(4-{[3-fluoro-5-(trifluoromethyl)phenyl]methyl}pyridin-2-yl)-4,5,6,7-tetrahydro-1H-benzotriazol-4-yl]acetamide;

N-(1-{4-[3-fluoro-5-(trifluoromethyl)phenoxy]pyridin-2-yl}-4,5,6,7-tetrahydro-1H-benzotriazol-4-yl) acetamide;

1-(4-{[3-fluoro-5-(trifluoromethyl)phenyl]methyl}pyridin-2-yl)-N-methyl-4,5,6,7-tetrahydro-1H-benzotriazol-4-amine;

1-(4-{[3-fluoro-5-(trifluoromethyl)phenyl]methyl}pyridin-2-yl)-N-(2-methoxyethyl)-4,5,6,7-tetrahydro-1H-benzotriazol-4-amine;

1-(4-{[3-fluoro-5-(trifluoromethyl)phenyl]methyl}pyridin-2-yl)-N-(oxetan-3-yl)-4,5,6,7-tetrahydro-1H-benzotriazol-4-amine;

1-(4-{[3-fluoro-5-(trifluoromethyl)phenyl]methyl}pyridin-2-yl)-N-(oxolan-3-yl)-4,5,6,7-tetrahydro-1H-benzotriazol-4-amine;

N-[1-(4-{[3-(trifluoromethyl)phenyl]methyl}pyridin-2-yl)-4,5,6,7-tetrahydro-1H-benzotriazol-4-yl]acetamide;

N-[1-(4-{[3-(difluoromethoxy)-5-fluorophenyl]methyl}pyridin-2-yl)-4,5,6,7-tetrahydro-1H-benzotriazol-4-yl]acetamide;

N-[1-(4-{[3-(difluoromethyl)-5-fluorophenyl]methyl}pyridin-2-yl)-4,5,6,7-tetrahydro-1H-benzotriazol-4-yl]acetamide;

N-[1-(4-{[3-fluoro-5-(fluoromethyl)phenyl]methyl}pyridin-2-yl)-4,5,6,7-tetrahydro-1H-benzotriazol-4-yl]acetamide;

1-(4-(3-fluoro-5-(trifluoromethyl)phenoxy) pyridin-2-yl)-4,5,6,7-tetrahydro-1H-benzo[d][1,2,3]triazol-4-amine;

1-(4-(3-(trifluoromethyl)benzyl)pyridin-2-yl)-4,5,6,7-tetrahydro-1H-benzo[d][1,2,3]triazol-4-amine;

1-(4-(3-(difluoromethoxy)-5-fluorobenzyl)pyridin-2-yl)-4,5,6,7-tetrahydro-1H-benzo[d][1,2,3]triazol-4-amine;

(4R)-1-(4-{[3-fluoro-5-(trifluoromethyl)phenyl]methyl}pyridin-2-yl)-4,5,6,7-tetrahydro-1H-benzotriazol-4-amine;

(4S)-1-(4-{[3-fluoro-5-(trifluoromethyl)phenyl]methyl}pyridin-2-yl)-4,5,6,7-tetrahydro-1H-benzotriazol-4-amine;

N-[(4R)-1-(4-{[3-fluoro-5-(trifluoromethyl)phenyl]methyl}pyridin-2-yl)-4,5,6,7-tetrahydro-1H-benzotriazol-4-yl]acetamide;

N-[(4S)-1-(4-{[3-fluoro-5-(trifluoromethyl)phenyl]methyl}pyridin-2-yl)-4,5,6,7-tetrahydro-1H-benzotriazol-4-yl]acetamide;

N-[(4R)-1-(4-{[3-(difluoromethyl)-5-fluorophenyl]methyl}pyridin-2-yl)-4,5,6,7-tetrahydro-1H-benzotriazol-4-yl]acetamide;

N-[(4S)-1-(4-{[3-(difluoromethyl)-5-fluorophenyl]methyl}pyridin-2-yl)-4,5,6,7-tetrahydro-1H-benzotriazol-4-yl]acetamide;

or a salt thereof.

14. The compound according to claim 1, wherein said compound is:

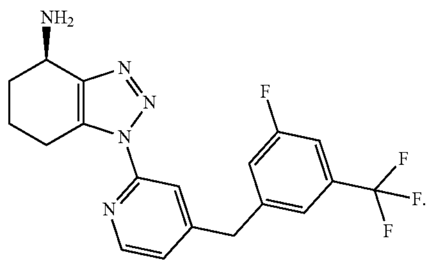 [SMILES: N[C@@H]1CCCc2c1nnn2-c1cc(Cc2cc(F)cc(C(F)(F)F)c2)ccn1]

15. A pharmaceutically acceptable salt of the compound as defined in claim 14.

16. The compound according to claim 1, wherein said compound is:

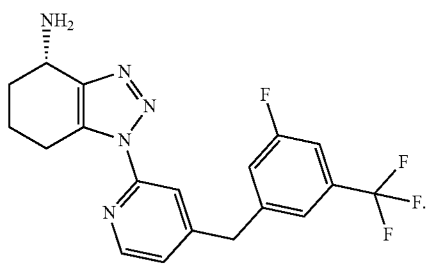 [SMILES: N[C@H]1CCCc2c1nnn2-c1cc(Cc2cc(F)cc(C(F)(F)F)c2)ccn1]

17. A pharmaceutically acceptable salt of the compound as defined in claim 16.

18. The compound according to claim 1, wherein said compound is:

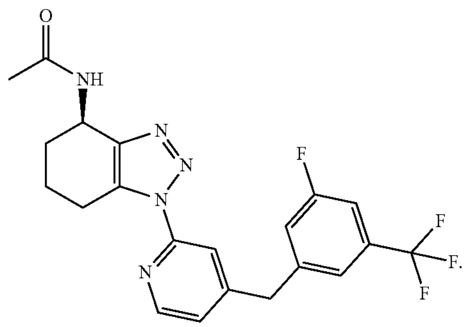 [SMILES: CC(=O)N[C@@H]1CCCc2c1nnn2-c1cc(Cc2cc(F)cc(C(F)(F)F)c2)ccn1]

19. A pharmaceutically acceptable salt of the compound as defined in claim 18.

20. The compound according to claim 1, wherein said compound is:

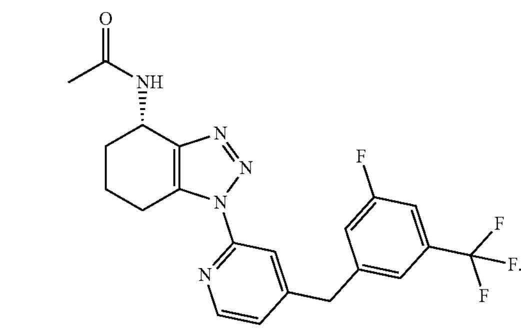 [SMILES: CC(=O)N[C@H]1CCCc2c1nnn2-c1cc(Cc2cc(F)cc(C(F)(F)F)c2)ccn1]

21. A pharmaceutically acceptable salt of the compound as defined in claim 20.

22. The compound according to claim 1, wherein said compound is:

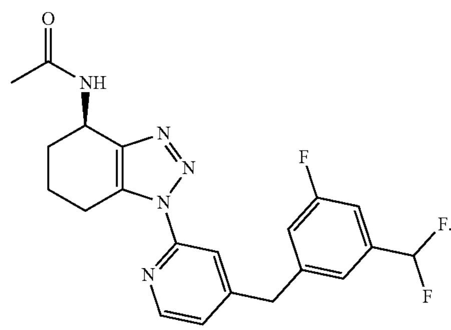 [SMILES: CC(=O)N[C@@H]1CCCc2c1nnn2-c1cc(Cc2cc(F)cc(C(F)F)c2)ccn1]

23. A pharmaceutically acceptable salt of the compound as defined in claim 22.

24. The compound according to claim 1, wherein said compound is:

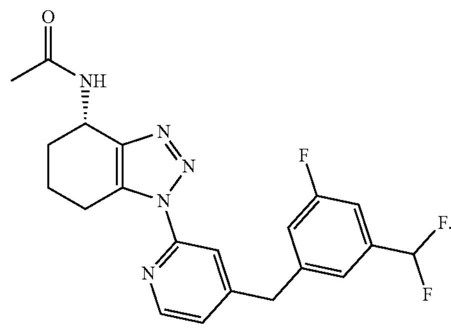 [SMILES: CC(=O)N[C@H]1CCCc2c1nnn2-c1cc(Cc2cc(F)cc(C(F)F)c2)ccn1]

25. A pharmaceutically acceptable salt of the compound as defined in claim 24.

26. The compound according to claim 1, wherein said compound is:

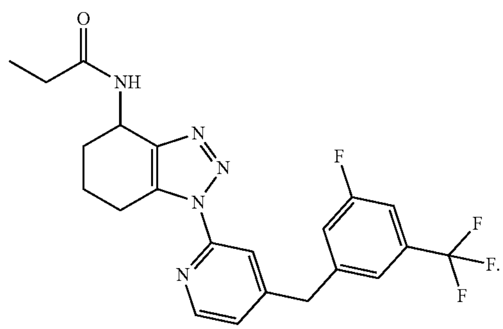 [SMILES: CCC(=O)NC1CCCc2c1nnn2-c1cc(Cc2cc(F)cc(C(F)(F)F)c2)ccn1]

27. A pharmaceutically acceptable salt of the compound as defined in claim 26.

28. The compound according to claim 1, wherein said compound is:

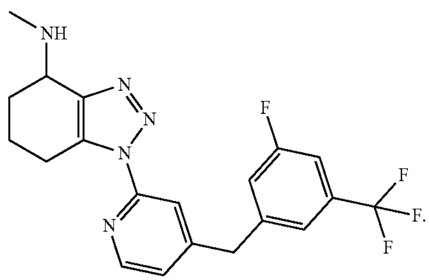 [SMILES: CNC1CCCc2c1nnn2-c1cc(Cc2cc(F)cc(C(F)(F)F)c2)ccn1]

29. A pharmaceutically acceptable salt of the compound as defined in claim 28.

30. The compound according to claim 1, wherein said compound is:

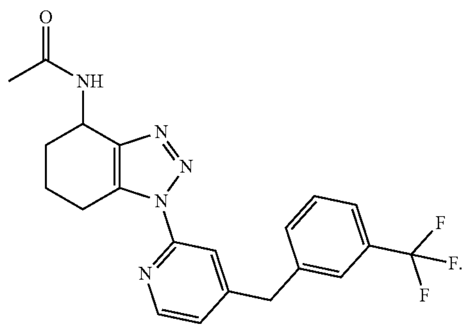 [SMILES: CC(=O)NC1CCCc2c1nnn2-c1cc(Cc2cccc(C(F)(F)F)c2)ccn1]

31. A pharmaceutically acceptable salt of the compound as defined in claim 30.

32. The compound according to claim 1, wherein said compound is:

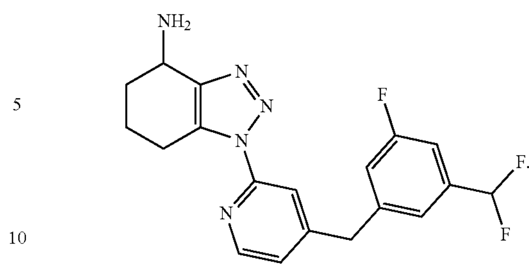

33. A pharmaceutically acceptable salt of the compound as defined in claim 32.

34. The compound according to claim 1, wherein said compound is:

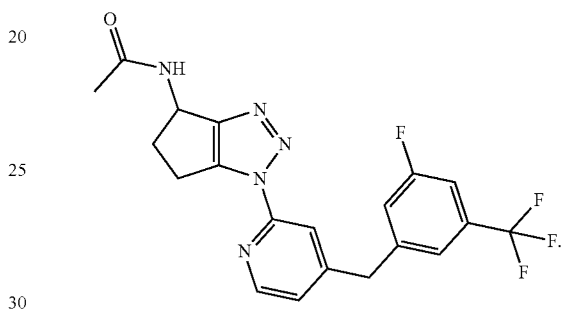

35. A pharmaceutically acceptable salt of the compound as defined in claim 34.

36. The compound according to claim 1, wherein said compound is:

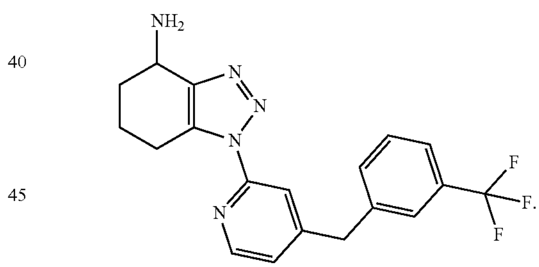

37. A pharmaceutically acceptable salt of the compound as defined in claim 36.

38. A pharmaceutical composition comprising an effective amount of a compound as defined in claim 1 and a pharmaceutically acceptable excipient.

* * * * *